United States Patent [19]

Gisler et al.

[11] Patent Number: 5,760,215

[45] Date of Patent: Jun. 2, 1998

[54] FIBRE-REACTIVE DYESTUFFS

[75] Inventors: Markus Gisler, Rheinfelden, Switzerland; Roland Wald, Huningue, France

[73] Assignee: Clariant Finance (BVI) Limited, Tortola, Virgin Islands (Br.)

[21] Appl. No.: 659,461

[22] Filed: Jun. 6, 1996

[30] Foreign Application Priority Data

Jun. 7, 1995 [GB] United Kingdom ............... 9511485
Dec. 13, 1995 [GB] United Kingdom ............... 9525473

[51] Int. Cl.$^6$ .................... C07D 487/22; C09B 62/036
[52] U.S. Cl. .................... 540/140; 534/619; 534/621; 534/620; 534/627; 534/628
[58] Field of Search ............... 540/140, 131, 540/133, 135; 534/619, 628

[56] References Cited

U.S. PATENT DOCUMENTS

| | | | |
|---|---|---|---|
| 4,576,755 | 3/1986 | Mischke et al. | 8/661 |
| 4,879,372 | 11/1989 | Morimitsu et al. | 534/618 |
| 4,900,812 | 2/1990 | Moser et al. | 534/627 |
| 5,126,443 | 6/1992 | Moser et al. | 540/125 |
| 5,455,334 | 10/1995 | Wald | 534/624 |
| 5,556,966 | 9/1996 | Kimura et al. | 540/140 |
| 5,608,053 | 3/1997 | Thetford et al. | 540/140 |

FOREIGN PATENT DOCUMENTS 41 02 777   6/1992   Germany.

*Primary Examiner*—John M. Ford
*Assistant Examiner*—Pavanaram K. Sripada
*Attorney, Agent, or Firm*—Scott E. Hanf; Hesna J. Pfeiffer

[57] ABSTRACT

The invention is related to compounds of formula (I)

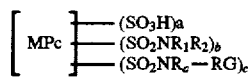

their salts and mixtures thereof wherein the symbols are as defined in the specification are useful as fibre-reactive dyestuffs for dyeing or printing hydroxy-group-containing or nitrogen-containing organic substrates.

12 Claims, No Drawings

FIBRE-REACTIVE DYESTUFFS

This application is concerned with phthalocyanine fibre-reactive dyestuffs and methods of producing the same.

The invention provides in one of its aspects compounds of formula (I)

$$\left[ MPc \begin{array}{l} -(SO_3H)_a \\ -(SO_2NR_1R_2)_b \\ -(SO_2NR_a-RG)_c \end{array} \right]$$

their salts and mixtures thereof
wherein, $R_1$ is hydrogen, or a hydrocarbon group having from 1 to 8 carbon atoms optionally comprising a hetero-atom or atoms, i.e oxygen nitrogen or sulphur atoms, in particular $C_{1-4}$ alkyl optionally substituted with an hydroxyl group, e.g. methyl, ethyl and hydroxyethyl $R_2$ is, independently of $R_1$, any of the significances of $R_1$, or is a group —$A_nSO_2$—B or —$A_nSO_2$—B' wherein B is selected from any of the groups according to the formula —CH=CH$_2$, —CH$_2$CH$_2$—Y, —CH=CH—Y or —CH(CH$_2$Y)—CH$_2$Y wherein Y represents a hydroxyl group or a group selected from halogen, e.g. chlorine or bromine, —OSO$_3$H or —SO$_3$H, —OPO$_3$H$_2$, —SSO$_3$H, —OCOCH$_3$, —OCOC$_6$H$_5$, —OCO(CH$_2$)$_2$—COOH, —OCO—CH=CH—COOH, —OCO—C$_6$H$_4$—COOH, —OCO—COOH, —OSO$_2$CH$_3$, a quaternary nitrogen group, e.g., —$^+$N(CH$_3$)$_3$ and a pyridinium ion or bivalent groups —OCO—COO—, —OCO—(CH$_2$)$_2$—COO—, —OCO—CH=CH—COO— and OCO—C$_6$H$_4$—COO—.

B' is —(CH$_2$)$_2$—OSO$_3$H and $A_n$ is $A_1$ to $A_3$ wherein $A_1$ is a group $$-R_3-\overset{m}{\underset{p}{\bigcirc}}*$$

wherein * is a bond connected to SO$_2$B and $R_3$ is a direct bond or is —(CH$_2$)$_2$—, $A_2$ is a group $A_1$, in which $R_3$ is a direct bond, or is an alkylene or oxyalkylene group having from 2 to 4 carbon atoms, and $A_3$ is a group represented by the formula $$(H, SO_3H)\overset{2}{\underset{4}{\bigcirc}}\overset{3}{-}N=N-\underset{OH}{\overset{(CH_3, COOH)}{\bigcirc}}-\underset{N}{\overset{N}{\parallel}}-\bigcirc*$$

(wherein * is a bond connected to SO$_2$B)

$R_1$, and $R_2$ together represent a divalent group, e.g. alkylene or aralkylene optionally bearing a heteroatom, i.e. oxygen, nitrogen or sulphur, preferably —(CH$_2$)$_2$—O—(CH$_2$)$_2$—, —(CH$_2$)$_{4-5}$— or —(CH$_2$)$_2$—N(R$_4$)—(CH$_2$)$_2$— wherein R$_4$ is an alkyl group having 1 to 4 carbon atom optionally substituted with a hydroxyl group, $R_a$ is hydrogen, alkyl having 1 to 4 carbon atoms, hydroxyalkyl having 2 to 4 carbon atoms or a group —$A_xSO_2$—B wherein B is as hereinabove defined and $A_x$ is defined below.

RG is a group containing a fibre-reactive group and is selected from —$A_xSO_2$—B or —D—NR$_{10}$Z wherein $A_x$ is represented by a divalent hydrocarbon group which may comprise oxygen, nitrogen or sulphur atoms and is preferably a divalent group chosen from an alkylene group optionally comprising an oxygen, nitrogen or sulphur atom or atoms, e.g.—(CH$_2$)—$_{2,3}$, —(CH$_2$)—$_2$O—(CH$_2$)—$_{2,3}$; an aza-alkylene group —(CH$_2$)$_2$—NR$_4$—(CH$_2$)$_2$—; an arylene group, for example $$-\underset{R_5}{\bigcirc}-$$

wherein $R_5$ represents a hydrogen atom, halogen atom, e.g. Cl or Br, an alkyl group having 1 to 4 carbon atoms, an alkoxy group having 1 to 4 carbon atoms, —SO$_3$H or —COOH, more preferably H, —COOH or SO$_3$H, most preferably H or SO$_3$H; a heterocyclic group, e.g. a phenylene azophenylpyrazolaryl group according to the formula $$-\bigcirc-N=N-\underset{\underset{R_5}{\bigcirc}}{\overset{R_6}{\underset{OH}{\parallel}}}-N=N-\bigcirc-$$

wherein $R_5$ is as hereinbefore defined and $R_6$ is a methyl group or a group —COOH; or a triazine group according to the formula $$-R_7-\underset{R_8}{N}-\underset{N}{\overset{L}{\underset{\parallel}{\bigvee}}}-\underset{R_8}{N}-R_7$$

wherein L is a hydroxyl group, a halogen atom, e.g. F, Cl or Br, or an amino group NR$_1$R'$_2$ wherein R'$_2$ is any of the significances of R$_1$ or together with R$_1$ is divalent group, e.g. alkylene or aralkylene optionally bearing a hetero atom i.e. oxygen, nitrogen or sulphur, or a pyridinium group $$-^+N\underset{}{\bigcirc}(R_9)_{1,2}$$

wherein $R_9$ is —SO$_3$H or —COOH, preferably L is a hydroxyl group, F, Cl or a group

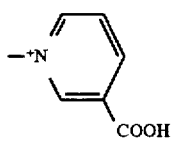

$R_7$ is a divalent group selected from alkylene, oxaalkylene, arylene or aralkylene, preferably $R_7$ is an alkylene group having 2 to 6 carbon atoms, 3-oxapentylene or a phenylene group substituted at its meta or para- position with, e.g. an alkyl group, alkoxy group, COOH or $SO_3H$.

$R_8$ is a hydrogen atom, an alkyl group having 1 to 4 carbon atoms, or a hydroxyalkyl group having 2 to 4 carbon atoms, preferably $R_8$ is a hydrogen atom, Z represents a heterocyclic fibre-reactive radical, e.g. halo-triazine or halo-pyrimidine having a labile fluorine or chlorine atom, $R_{10}$ is H or $CH_3$ and D represents a divalent group selected from

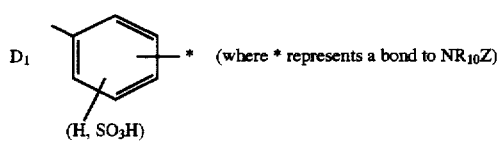

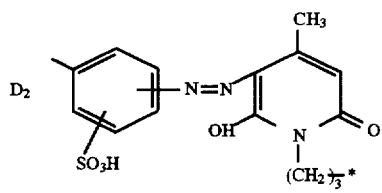

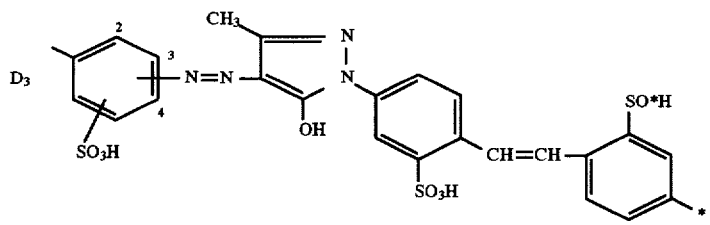

preferably when D is $D_2$, $R_{10}$ is $CH_3$

M is AlOH or AlCl

Pc is a phthalocyanine radical a is 1, 2 or 3 b is 0, 1, 2 or 3 c is 0, 1 or 2 and a+b+c has a value which is greater than or equal to 3 and less than or equal to 4 and b and c cannot be zero at the same time, the compounds being selected from those satisfying the following conditions:

i) when c is 1 or 2, RG is —D—$NR_{10}Z$ and D is $D_1$, then b is 1 or 2, $R_2$ is —$A_2SO_2$—B and $R_a$ is not $A_xSO_2$—B, ii) when c is 1, RG is —D—$NR_{10}Z$ and D is $D_2$ or $D_3$, then b is 1 or 2, $R_2$ is —$A_2SO_2$—B and $R_a$ is not $A_xSO_2$—B, iii) when c is 1, RG is —D—$NR_{10}Z$ and D is $D_1$ then b is 1, $R_2$ is —$A_3SO_2$—B and $R_a$ is not $A_xSO_2$—B, iv) when c is 1 and RG is $A_xSO_2$—B, then $R_2$ is, independently of $R_1$, any of the significances of $R_1$, b is 0, 1 or 2 and v) when c is zero, then b is 1, 2 or 3, $R_2$ is $A_1SO_2$—B'

The heterocyclic fibre-reactive radical of the compounds according to the invention are preferably selected from those fibre-reactive radicals $Z_1$ to $Z_9$ defined hereinbelow

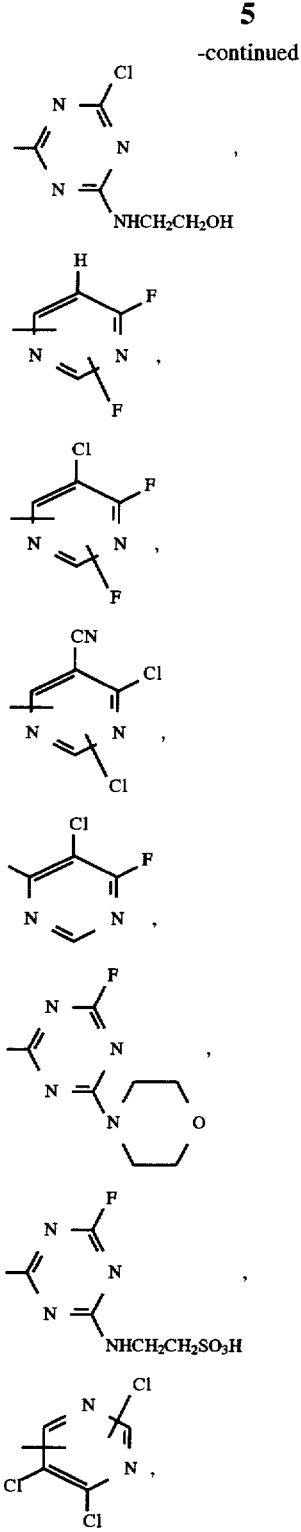

The fibre-reactive radical is preferably $Z_1$, $Z_3$ or $Z_7$, more preferably $Z_1$. In a dyeing process, the nature of the group Z employed depends upon the temperature at which the dyeing is to be carried out. When the dyeing temperature is from 30° to 80° C., in particular 50° to 80° C., more particularly 50° to 60° C., it is appropriate to select Z as $Z_3$, $Z_4$, $Z_5$ or $Z_8$, in particular $Z_3$ or $Z_7$. When the dyeing temperature is from 80° to 100° C., it is appropriate to select $Z_1$, $Z_2$, $Z_6$ or $Z_9$, in particular $Z_1$.

In a preferred embodiment of the invention there are provided compounds according to the formula (Ia)

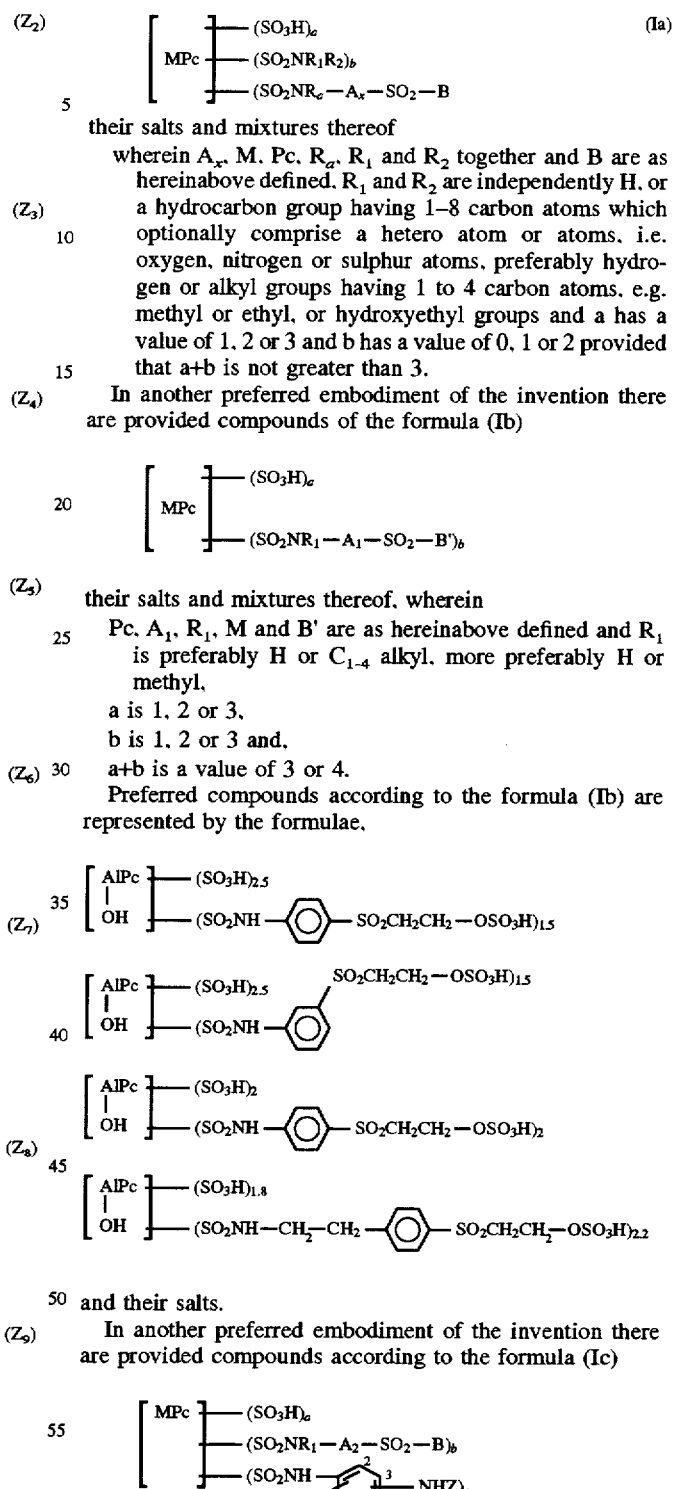

their salts and mixtures thereof wherein $A_x$, M, Pc, $R_a$, $R_1$ and $R_2$ together and B are as hereinabove defined. $R_1$ and $R_2$ are independently H, or a hydrocarbon group having 1–8 carbon atoms which optionally comprise a hetero atom or atoms, i.e. oxygen, nitrogen or sulphur atoms, preferably hydrogen or alkyl groups having 1 to 4 carbon atoms, e.g. methyl or ethyl, or hydroxyethyl groups and a has a value of 1, 2 or 3 and b has a value of 0, 1 or 2 provided that a+b is not greater than 3.

In another preferred embodiment of the invention there are provided compounds of the formula (Ib)

their salts and mixtures thereof, wherein

Pc, $A_1$, $R_1$, M and B' are as hereinabove defined and $R_1$ is preferably H or $C_{1-4}$ alkyl, more preferably H or methyl, a is 1, 2 or 3, b is 1, 2 or 3 and, a+b is a value of 3 or 4.

Preferred compounds according to the formula (Ib) are represented by the formulae, and their salts.

In another preferred embodiment of the invention there are provided compounds according to the formula (Ic)

their salts and mixtures thereof wherein the symbols Pc, Z, $A_2$, $R_1$ and B are as hereinabove defined, $R_{11}$ is hydrogen or —$SO_3H$, a is 1 or 2 c is 1 or 2 and b is 1 or 2, provided that a+b+c is 3 or 4.

With respect to the compounds (Ic), a preferred group $A_2$ is represented by phenylene, —$(CH_2)_n$—, wherein n is 2 or 3 or —$(CH_2)_2$—O—$(CH_2)_2$— and a preferred group B is represented by —CH$_2$CH$_2$OSO$_3$H, CH$_2$CH$_2$Cl or —CH=CH$_2$, more preferably A$_2$ is phenylene when B is —CH$_2$CH$_2$OSO$_3$H and A$_2$ is —(CH$_2$)$_n$—, wherein n is 2 or 3 or —(CH$_2$)$_2$—O—(CH$_2$)$_2$— when B is —CH$_2$CH$_2$Cl or —CH=CH$_2$.

It is preferred that the group —NR$_{10}$Z is located at the 3- or 4- position. Similarly, when A$_2$ is a phenylene group it is preferred if the group —SO$_2$B is located in the 3- or 4-position.

In a further preferred embodiment of the invention there are provided compounds according to the formula (Id)

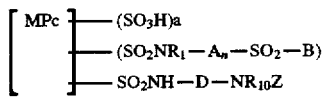

their salts and mixtures thereof wherein the symbols Z, B, Pc, M, A$_n$, R$_{10}$ are as hereinabove described, D is D$_2$ or D$_3$ and a has a value of 1 or 2.

In preferred compounds (Id) the group —SO$_2$B is in the 3- or 4-position.

In more preferred compounds (Id), the group A$_n$ is A$_1$, D is D$_2$, B is —CH$_2$CH$_2$OSO$_3$H or —CH=CH$_2$ and Z is Z$_5$; A$_n$ is A$_1$, D is D$_3$, B is —CH$_2$CH$_2$OSO$_3$H and Z is Z$_5$ or Z$_9$.

It is to be understood that the compounds of the formula (I) are obtained as isomeric mixtures according to the number and position of the substituents attached to the phthalocyanine ring. Particularly preferred isomeric mixtures contain not less than 1 and not more than 2 reactive groups per molecule on average, e.g. 1.0, 1.5 or 2.0. If desired, one could resolve the mixtures into isomerically pure forms employing conventional separation techniques.

When compounds according to the formula I are in the salt form, the cation associated with a sulpho-group may be any of the known non-chromophoric cations. Preferred are the alkali metal cations, for example sodium or potassium. Cations associated with sulpho-groups may be the same or different, i.e. the compounds of formula (I) can be in the mixed-salt form.

The compounds (Ia) are formed according to a process comprising the steps of reacting a compound of the formula (IIa)

[MPc+(SO$_2$Cl)a+b+1]    (IIa)

with one equivalent of HNR$_a$—A$_x$—SO$_2$—B and b equivalents of HNR$_1$R$_2$ and thereafter hydrolysing the remaining SO$_2$Cl group or groups, wherein R$_2$ is selected from hydrogen, a saturated hydrocarbon group having 1 to 8 carbon atoms which optionally comprise a hetero atom or atoms, i.e. oxygen, nitrogen or sulphur atoms. Preferred groups R$_1$ and R$_2$ are hydrogen or alkyl groups having 1 to 4 carbon atoms, e.g. methyl or ethyl, or hydroxyethyl groups, a is 1, 2 or 3, b is 0,1 or 2 and a+b is not greater than 3.

The sequence in which the reagents HNR$_a$—A$_x$—SO$_2$—B and HNR$_1$R$_2$ are reacted is critical when A$_x$ contains aromatic functionality. In any case, it is generally preferred if the reaction proceeds initially with the reaction of one equivalent of HNR$_a$—A$_x$—SO$_2$—B followed by b equivalents of HNR$_1$R$_2$.

Reaction of a compound IIa with HNR,—A$_x$—SO$_2$—B is preferably carried out at a pH of from 3 to 7 and at a temperature of from 0° to 40° C. Reaction of HNR$_1$R$_2$ with the product of the afore-mentioned reaction is preferably conducted at a pH of from 5 to 9 and at a temperature of from 0° to 40° C. Preferably, the reactions are carried out in aqueous media.

The hydrolysis step is carried out in an aqueous medium under acidic conditions and is preferably carried out at a pH of from 0 to 4 and at a temperature of 0° to 20° C.

When the group A$_x$ contains an azo chromophore it is preferred to employ a modification of the process hereinabove described comprising the steps of reacting a compound of the formula (IIa)

[MPc+(SO$_2$Cl)a+b+1]    (IIa)

with one equivalent of HNR$_a$—A$_x$'—NH$_2$ and b equivalents of HNR$_1$R$_2$ and hydrolysing the remaining SO$_2$Cl group or groups to form an intermediate compound according to the formula (IIIa), wherein R$_2$ is selected from hydrogen, a saturated hydrocarbon group having 1 to 8 carbon atoms which optionally comprise a hetero atom or atoms, i.e. oxygen, nitrogen or sulphur atoms. Preferred groups R$_1$ and R$_2$ are hydrogen or alkyl groups having 1 to 4 carbon atoms, e.g. methyl or ethyl, or hydroxyethyl groups.

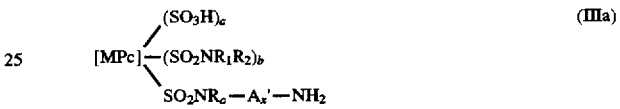

(IIIa)

wherein A$_x$'—NH$_2$ represents a precursor of A$_x$ such that when A$_x$'—NH$_2$ is diazotised and the diazonium salt thus formed is coupled with a suitable coupling component the group —A$_x$—SO$_2$—B is formed.

The primary amino group connected to A$_x$' of the compound (IIIa) is diazotised according to conventional methods and the resultant diazonium salt coupled with a suitable coupling component, for example

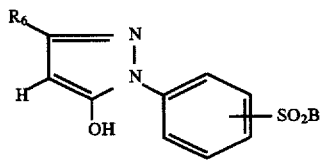

to form a compound according to the formula (Ia).

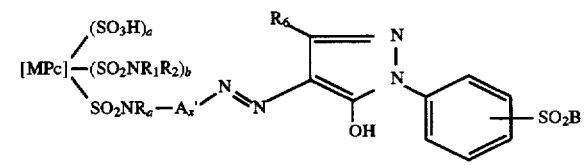

wherein A$_x$' represents

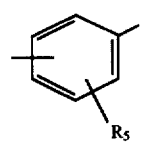

Similarly, when the group A$_x$ contains a triazine group, an intermediate compound (IIIa)

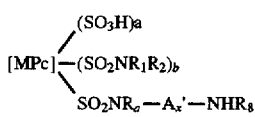

is formed which is thereafter reacted with a compound according to the formula

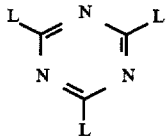

wherein at least two L are represented by fluorine or chlorine, more preferably fluorine and $A_x'$ represents $R_7$ to form a compound

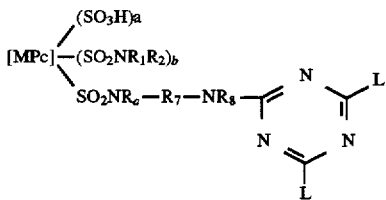

which in turn is reacted with one equivalent of $HNR_8$—$R_7$—$SO_2B$ according to conventional methods to form a compound according to the formula (Ia).

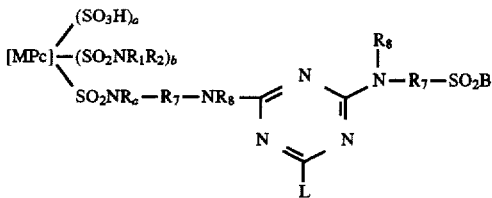

Compounds according to the formula (Ia) may be isolated from the reaction medium according to known methods, for example, salting out with an alkali metal salt, filtering and drying optionally in vacuo at slightly elevated temperature.

The compounds (Ib) are formed according to a process comprising the steps of reacting the compound

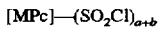 (IIb)

with the compound

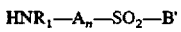 (IIIb)

and thereafter hydrolysing the remaining —$SO_2Cl$ group or groups wherein B' is as hereinabove defined and a+b is 3 or 4.

Reaction of a compound (IIb) with compound (IIIb) is preferably carried out at a pH of from 3 to 7 and at a temperature of from 0° to 40° C. Preferably the reaction is carried out in an aqueous medium.

The hydrolysis step is carried out in an aqueous medium under acidic conditions most preferably at a pH of 0 to 4 and a temperature of 0° to 20° C.

Compounds according to the formula (Ib) can be isolated from the reaction medium according to known methods, for example, by salting out with an alkali metal salt and thereafter filtering and drying optionally under vacuum.

The compounds according to the formula (Ic) are formed according to a process comprising the steps of reacting a compound having the formula (IIa) hereinabove defined with b equivalents of $HNR_1$—$A_2$—$SO_2B$ and c equivalents of a compound according to the formula (IIc)

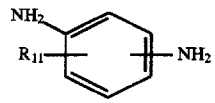

hydrolysing the remaining $SO_2Cl$ group or groups and thereafter condensing the free amino group with a compound Z—Cl or Z—F.

Preferably, when Z is the chloro- or fluoro- triazine corresponding to $Z_1$, $Z_2$, $Z_7$ or $Z_8$, the process comprises the additional step of reacting the condensation product with one equivalent of ammonia (when Z is $Z_1$) or the amine corresponding to the amine radical of $Z_2$, $Z_7$ or $Z_8$.

The process conditions for condensing the amine $HNR_1$—$A_2$—$SO_2B$ and the hydolysis of any $SO_2Cl$ groups are conventional in the art and are preferably as hereinabove described.

The compounds according to the formula (Id) are formed according to a process comprising the steps of reacting a compound having the formula (IIa) hereinabove defined with b equivalents of $HNR_1$—$A_n$—$SO_2B$ and c equivalents of a compound according to the formula (IId)

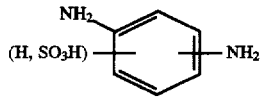

hydrolysing the remaining $SO_2Cl$ group or groups and thereafter diazotising the free amino group before reacting the diazonium salt in a coupling reaction with a coupling component selected from

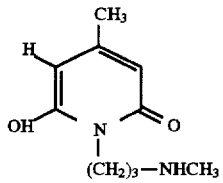

or

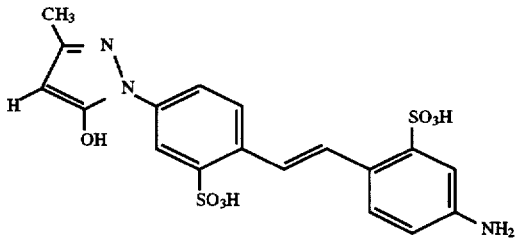

and thereafter reacting the amino group on the radical of the coupling component with a compound Z—F or Z—Cl.

The reaction conditions for condensing the amine $HNR_1$—$A_2$—$SO_2B$ and the hydolysis of any $SO_2Cl$ groups are conventional in the art and are preferably as hereinabove described. The reaction conditions for the formation of the diazonium salt are also conventional in the art.

Depending on the reaction and isolation conditions, compounds of the formula (I) may be obtained in free-acid or preferably in salt form or mixed salt form, containing, for example, one or more of the above mentioned cations. Compounds of the formula (I) may be converted from the free-acid form to the salt-form and vice versa using techniques known in the art.

Compounds according to the formula (I) their salts or a mixture thereof are useful as fibre-reactive dyestuffs. They are suitable for dyeing or printing hydroxy-group-containing or nitrogen-containing organic substrates.

Accordingly, in another aspect of the invention there is provided a process of dyeing or printing hydroxy-group-containing or nitrogen-containing organic substrates wherein the dyeing or printing is carried out with compounds according to the formula (I), their salts or with mixtures thereof.

Preferred substrates may be selected from leather, and fibrous materials comprising natural or synthetic polyamides and more particularly natural or regenerated cellulose, e.g., cotton, viscose and spun rayon. The most preferred substrates are textile materials consisting of or containing cotton.

The compounds of formula (I), their salts or mixtures thereof may be employed in dyebaths or in printing pastes and dyeing or printing may be effected in accordance with methods known in the fibre-reactive dyestuffs field, for example, the exhaust dyeing process, padding, e.g., Pad-steam, pad-thermofix, pad-dry, pad-batch, pad-jig and pad-roll and conventional printing or ink-jet methods. Preferably dyeings are carried out using the exhaust dyeing method at temperatures within the range of 30° to 95° C., more preferably 40° to 70° C. A goods to liquor ratio of from 1:20 to 1:4, more preferably 1:10 to 1:6 is used.

In yet another aspect of the invention there is provided the use of compounds according to the formula (I), their salts or mixtures thereof in dyeing or printing substrates as hereinabove described.

The compounds according to the invention and their salts have good compatibility with known fibre-reactive dyestuffs. Accordingly, the compounds of the invention, their salts or mixtures thereof may be used alone in a dyeing or printing process or as a component in a combination dyeing or printing composition comprising other reactive dyestuffs of the same class, that is, reactive dyes which possess comparable dyeing properties, e.g., fastness properties and the extent of the ability to exhaust from a dyebath onto a substrate. In particular, the dyestuffs of the invention may be employed in conjunction with certain other dyestuffs having suitable chromophores and the same or other suitable reactive groups, the proportions of a particular dyestuff in such a composition being dictated by the particular shade which is to be produced.

Compounds of the formula (I) and their salts display high exhaust and fixation yields. Moreover, any unfixed dyestuff is easily washed off the substrate. The build-up power of the compounds and their salts is also good. Dyeings and prints obtained exhibit good light fastness properties and general wet fastnesses such as fastness to washing, sea water and sweat. They are also resistant to oxidative influences, e.g. chlorinated water, hypochlorite bleach and peroxide, percarbonate or perborate containing washing liquors.

In another aspect of the invention there is provided an hydroxy-group-containing or nitrogen-containing organic substrate dyed or printed with compounds of formula (I), their salts or a mixture therof.

There now follows a series of examples which serve to illustrate the invention. In the examples, all parts are expressed as parts by weight, all temperatures are expressed as degrees celsius unless specifically indicated to the contrary and λmax/nm are measured in water.

EXAMPLE 1

20 parts of PcAlCl. 2H$_2$O were stirred in 140 parts of chlorosulphonic acid for 30 minutes at 20° to 25° C. The reaction mixture was then heated to 135° to 140° C. over 2 hours. After 4 hours the reaction mixture was cooled to room temperature using, an ice bath. The suspension thus formed was filtered and washed in ice water to remove excess acid.

97 parts of the product formed by the above reaction was stirred in 300 parts of water and 100 parts of ice. Thereafter, a solution of 17.2 parts of (2'-amino ethane-1'-sulfonyl)-2-chloroethane in 100 parts of ice water was added. The pH of the resultant solution which was 1–2 was increased to 4–5 with 20% sodium hydroxide and thereafter left for 15 hours at a temperature of from 0° to 5° C. The resultant dyestuff was salted out with sodium chloride, filtered and dried at a temperature of from 40° to 50° C.

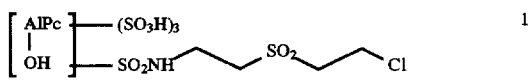

The dyestuff dyed cellulosic material, in particular cotton, to brilliant green shades with excellent wet fastness.

EXAMPLE 2

The dyestuff of Example 1 was dissolved in 0.1N sodium hydroxide. Thereafter the mixture was neutralised and the product was salted-out with sodium chloride to provide the vinyl sulphone (2) .

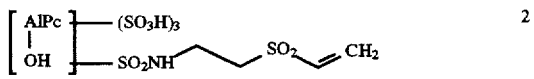

EXAMPLE 3a 97 parts of the chloroaluminium phthalocyanine sulphochloride obtained by a process described in the first paragraph of Example 1 was stirred in 300 parts of water and 100 parts of ice and thereafter was added a solution of 16.7 parts of (2'-aminopropane-1'-sulphonyl)-ethane-2-ol in 100 parts of ice water. The pH of the resultant solution which was 1–2 was adjusted to 7 with 20% sodium hydroxide and the mixture reacted for 4 hours at a temperature of from 0° to 5° C.

7 parts of a 25% ammoniacal solution was added to the reaction mixture and the pH was maintained at 7 with 20% sodium hydroxide solution. The reaction mixture was then left for a further 10 hours without cooling whereupon the pH increased to 10–11. The reaction mixture was then stirred for a further 2 hours at 60° C. to form the product 3a as a precipitate which could be filtered off. Compound 3a, was isolated in its sodium salt form.

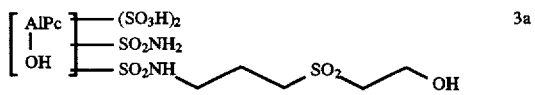

The compound 3a was converted into its sulphuric acid half ester by dissolving it in sulphuric acid. The resultant solution was stirred for one hour before being poured onto crushed ice. The pH was adjusted to 4 to 5 by adding sodium carbonate and the reactive dye 3b was isolated by spray drying.

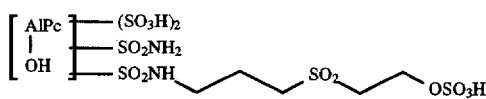

This dyestuff dyed cotton to a brilliant green shade and dyeing displayed high fastness properties.

EXAMPLES 4–23

The following compounds were obtained by processes analogous to the processes described in Examples 1 to 3.

This dyestuff dyed cotton to brilliant green shades and dyeings displayed good fastness properties.

EXAMPLE 25

By dissolving dyestuff 24 in 0.1N sodium hydroxide and thereafter neutralising and isolating the product obtained therefrom, dyestuff 25 was formed.

TABLE 1

$$\left[\begin{array}{c} AlPc \\ | \\ X \end{array}\right] \begin{array}{l} -(SO_3H)_a \\ -(SO_2N{}^{R_1}_{R_2})_b \\ -(SO_2N-A_x-SO_2B \\ \quad\quad R_a \end{array}$$

| Ex. | X  | a | b | NR₁R₂                                              | Rₐ                | Aₓ                                                      | B            |
|-----|----|---|---|----------------------------------------------------|-------------------|---------------------------------------------------------|--------------|
| 4   | OH | 2 | 1 | NH₂                                                | H                 | CH₂CH₂                                                  | CH=CH₂       |
| 5   | OH | 2 | 1 | NH₂                                                | H                 | CH₂CH₂                                                  | CH₂CH₂Cl     |
| 6   | OH | 2 | 1 | NH₂                                                | H                 | CH₂CH₂CH₂                                               | CH=CH₂       |
| 7   | OH | 2 | 1 | NH₂                                                | H                 | CH₂CH₂OCH₂CH₂                                           | CH₂CH₂Cl     |
| 8   | Cl | 2 | 1 | NH₂                                                | H                 | CH₂CH₂OCH₂CH₂                                           | CH=CH₂       |
| 9   | OH | 2 | 1 | NH₂                                                | CH₂CH₂SO₂CH=CH₂   | CH₂CH₂                                                  | CH=CH₂       |
| 10  | OH | 2 | 1 | NHCH₃                                              | H                 | CH₂CH₂                                                  | CH₂CH₂Cl     |
| 11  | OH | 2 | 1 | NH₂                                                | H                 | CH₂CH₂CH₂*<br>\|<br>CH₂CH<br>\|<br>SO₂CH₂CH₂Cl          | CH₂CH₂Cl     |
| 12  | OH | 2 | 1 | NH₂                                                | H                 | CH₂CH₂CH₂*<br>\|<br>CH₂CH<br>\|<br>SO₂CH=CH₂            | CH=CH₂       |
| 13  | OH | 2 | 1 | NHCH₂CH₂OH                                         | H                 | CH₂CH₂                                                  | CH=CH₂       |
| 14  | OH | 2 | 1 | NHCH₂CH₂OSO₃H                                      | H                 | CH₂CH₂                                                  | CH₂CH₂OSO₃H  |
| 15  | OH | 2 | 1 | NHCH₂CH₂SO₃H                                       | H                 | CH₂CH₂                                                  | CH=CH₂       |
| 16  | OH | 2 | 1 | N(CH₃)CH₂CH₂SO₃H                                   | H                 | CH₂CH₂                                                  | CH=CH₂       |
| 17  | OH | 2 | 1 | Morpholino                                         | H                 | CH₂CH₂                                                  | CH=CH₂       |
| 18  | OH | 2 | 1 | N(CH₃)CH₂CH₂OH                                     | H                 | CH₂CH₂OCH₂CH₂                                           | CH=CH₂       |
| 19  | OH | 2 | 1 | NHCH₂CH₂CH₂OH                                      | H                 | CH₂CH₂                                                  | CH=CH₂       |
| 20  | OH | 2 | 0 | —                                                  | H                 | CH₂CH₂OCH₂CH₂                                           | CH=CH₂       |
| 21  | OH | 2 | 0 | —                                                  | H                 | CH₂CH₂                                                  | CH=CH₂       |
| 22  | OH | 3 | 0 | —                                                  | H                 | CH₂CH₂CH₂                                               | CH₂CH₂Cl     |
| 23  | OH | 3 | 0 | —                                                  | H                 | CH₂CH₂OCH₂CH₂                                           | CH₂CH₂Cl     |

EXAMPLE 24

In an analogous process to that of Example 1, 28.1 parts of 3'-aminobenzosulphonyl)-2-sulphatoethane were substituted for (2'-aminoethane-1'-sulphonyl)-2-chloroethane used in Example 1 to obtain a dyestuff having the formula 24

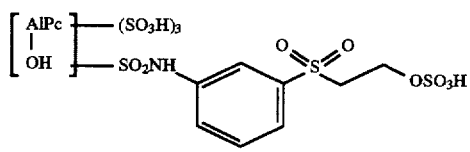

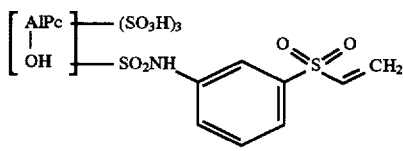

In the alternative, this dyestuff was formed directly by employing, in a method according to Example 1, 18.3 parts of (3'-aminobenzol-1'-sulphonyl)-ethene instead of (2'-aminoethane-1-sulphonyl)-2-chloroethane.

EXAMPLE 26 a

In a process analogous to Example 3a, one employed 20.1 parts of (4'-aminobenzol-1'-sulfonyl)-ethane-2-ol instead of (2'aminopropane-1'-sulfonyl)-ethane-2-ol to obtain the hydroxy compound 26a.

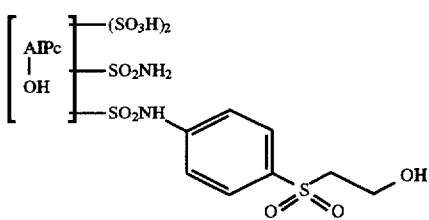

26a

EXAMPLE 26 b–d

Starting from the compound 26a, the reactive dye 26b was prepared by the following method: 106 parts of finely ground hydroxy dyestuff 23a were suspended in 500 parts of thionyl chloride and the mixture heated to the boil. After evolution of gas had ceased, excess thinyl chloride was distilled off. The residue was dissolved in water and the pH adjusted to 5–6 with sodium carbonate. The reactive dye 26b was salted out with sodium chloride.

The reactive dye 26c was obtained according to a process analogous with Example 3b. The vinyl sulphone dyestuff 26d was obtained according to a method described in Example 2.

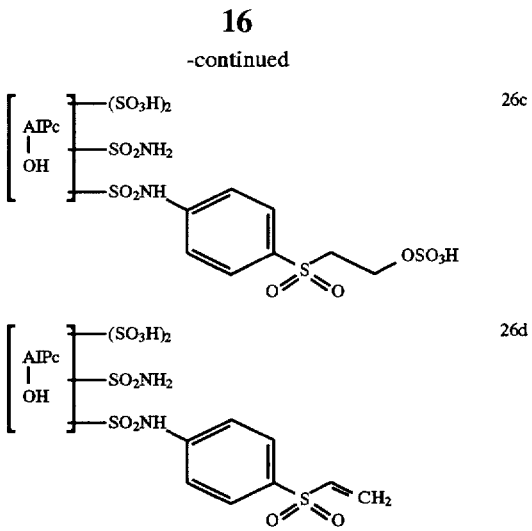

26c

26d

EXAMPLES 27–44

By processes analogous to those described above, other fibre-reactive dyestuffs 27–44 can be produced.

TABLE 2

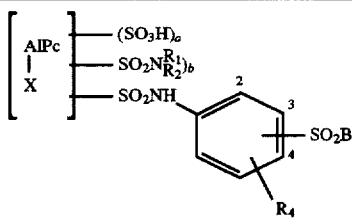

| Ex. | X | a | b | NR₁R₂ | R₄(Pos.) | SO₂B (Pos.) |
|---|---|---|---|---|---|---|
| 27 | OH | 2 | 1 | NH₂ | H | SO₂CH₂CH₂OSO₃H(3) |
| 28 | OH | 2 | 1 | NH₂ | H | SO₂CH=CH₂(3) |
| 29 | OH | 2 | 1 | NHCH₂CH₂OH | H | SO₂CH₂CH₂OSO₃H(4) |
| 30 | OH | 2 | 1 | NHCH₂CH₂OH | H | SO₂CH₂CH₂OSO₃H(3) |
| 31 | OH | 2 | 1 | NHCH₂CH₂SO₃H | H | SO₂CH₂CH₂OSO₃H(4) |
| 32 | OH | 2 | 1 | N(CH₃)CH₂CH₂SO₃H | H | SO₂CH₂CH₂OSO₃H(3) |
| 33 | OH | 2 | 1 | (morpholino) | H | SO₂CH=CH₂(4) |
| 34 | OH | 2 | 1 | N(CH₃)CH₂CH₂OH | H | SO₂CH₂CH₂OSO₃H(4) |
| 35 | OH | 2 | 1 | N(CH₃)CH₂CH₂OH | H | SO₂CH₂CH₂OSO₃H(3) |
| 36 | OH | 2 | 1 | NHCH₂CH₂(OH)CH₃ | H | SO₂CH₂CH₂OSO₃H(4) |
| 37 | OH | 2 | 1 | NHCH₂CH₂CH₂OH | H | SO₂CH₂CH₂OSO₃H(4) |
| 38 | OH | 2 | 1 | NHCH₂CH₂CH₂OH | H | SO₂CH₂CH₂OSO₃H(3) |
| 39 | OH | 2 | 1 | NHCH₂CH₂COOH | H | SO₂CH₂CH₂OSO₃H(4) |
| 40 | OH | 1 | 0 | — | SO₃H(2) | SO₂CH₂CH₂OSO₃H(5) |
| 41 | OH | 1 | 0 | — | SO₃H(2) | SO₂CH₂CH₂OSO₃H(4) |
| 42 | OH | 2 | 0 | — | H | SO₂CH₂CH₂OSO₃H(3) |
| 43 | OH | 2 | 0 | — | H | SO₂CH₂CH₂OSO₃H(4) |
| 44 | OH | 3 | 0 | — | H | SO₂CH₂CH₂OSO₃H(4) |

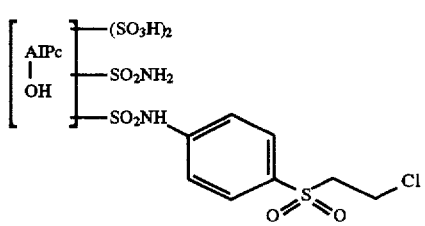

26b

EXAMPLE 45

97 parts of a chloro aluminium phthalocyanine tetrasulphochloride formed according to a method described in the first paragraph of Example 1 were stirred in 300 parts of water and 100 parts of ice. Thereafter, a solution of 14.5 parts of 1,3-diaminobenzol-monohydrochloride in 100 parts of ice water were added. The pH of the resultant solution which was 1–2 was adjusted to 4 with 20% sodium hydroxide and the reaction mixture was maintained at 0 to 5° C. for 4 hours.

Thereafter, the reaction mixture was adjusted to pH 10–11 by adding 20% sodium hydroxide and left to stir for a further 2 hours at 60° C. The product was salted out of solution using sodium chloride and the precipitate filtered to provide a product 45a in its sodium salt form.

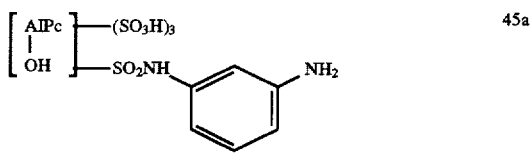

45a 97 parts of the dyestuff having a formula 45a was were suspended in a mixture of 500 parts of water and 25 parts of 30% hydrochloric acid. To the resultant suspension was added 100 parts of ice and diazotisation was effected by the addition of 7 parts of sodium nitrite. Thereafter, 36 parts of 1-(3'-sulphatoethylsulphonylphenyl)-3-methyl-5-pyrazolon were added to the aqueous suspension of the diazonium salt previously formed. The mixture was stirred at room temperature and maintained at a pH of 6 to 7 by addition of sodium carbonate until dye formation was completed. The dyestuff obtained had the following formula

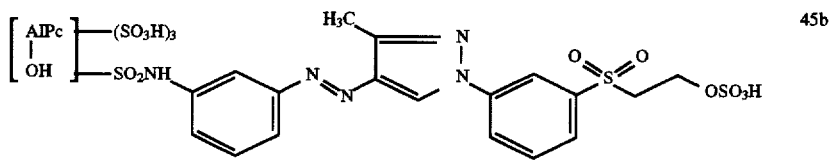

45b

The dyestuff dyed cotton to a brilliant green shade and dyeings displayed excellent fastness properties.

EXAMPLE 46

97 parts of the chloro aluminium phthalocyanine tetra-sulphochloride prepared according to the method described in the first paragraph of Example 1 was stirred in 300 parts of water and 100 parts of ice. To this solution there was added a solution of 14.5 parts of 1,3-diaminobenzol-monohydrochloride in 100 parts of ice water. The pH of the resultant solution was 1-2 and it was adjusted to a pH of 4 with 20% sodium hydroxide and allowed to stand for 4 hours at a temperature of of between 0° and 5° C.

Thereafter, 7 parts of a 25% ammoniacal solution was added to the reaction mixture, the pH was adjusted to 7 to 8 by adding 20% sodium hydroxide and the reaction mixture left for 10 hours. Thereafter, the pH was 10–11 and the reaction mixture was stirred at 60° C. for 2 hours whereupon the product was formed as a precipitate which was filtered off. The product 46a was obtained in its sodium salt form.

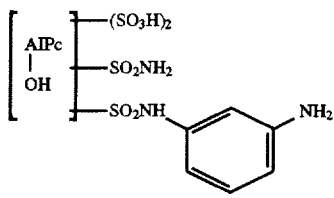

46a 97 parts of the amino dyestuff 46a was diazotised according to the method described in Example 45b. Thereafter, 36 parts of 1-(3'-sulphatoethylsulphonylphenyl)-5-pyrazolon-3-carboxylic acid were added to the aqueous suspension of the diazonium salt previously formed. The mixture was stirred at room temperature and maintained at a pH of 6 to 7 by addition of sodium carbonate until dye formation was completed. After the dyestuff was salted out using sodium chloride, filtered off and dried 129 parts of a product 46b was obtained as a dark blue-green powder.

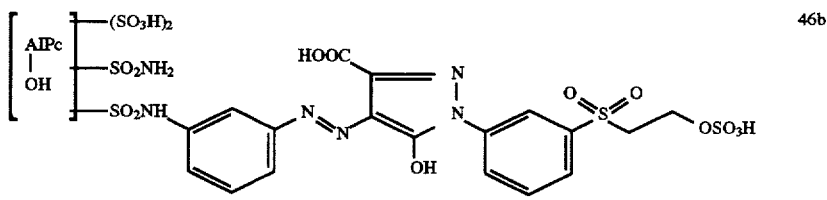

46b

This dyestuff dyed cotton in brilliant yellow-green shade and dyeings displayed excellent fastness properties.

EXAMPLE 47

When one substitutes 18.8 parts of 2,4-diaminobenzolsulphonic for 1,3-diaminobenzol-monohydrochlorid in a process analogous to Example 46 and couple with 36 parts of 1-(3'-sulphatoethylsulphonylphenyl)-3-methyl-5-pyrazolone one obtained a dyestuff 47.

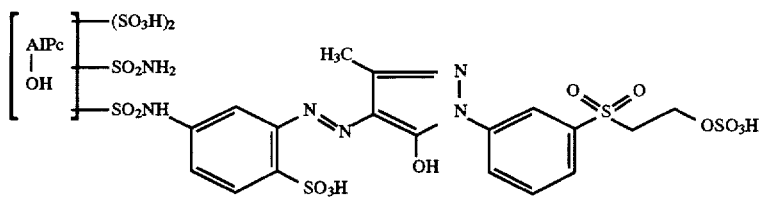

47

EXAMPLES 48–58

The following fibre-reactive dyestuffs were formed by employing processes analogous to those described in Examples 45 to 47.

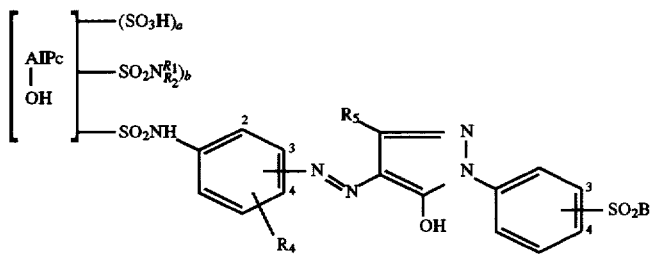

EXAMPLE 60

97 parts of the amino dyestuff 46a was mixed in 600 parts of ice water and 13.5 parts of 2,4,6-trifluorotriazine were added at a temperature of from −5° to −10° C. The solution

TABLE 3

| Ex. | X  | a | b | NR$_1$R$_2$ | R$_4$ (Pos.) | —N=N Pos. | R$_5$ | SO$_2$B (Pos.) |
|-----|----|---|---|-------------|--------------|-----------|-------|----------------|
| 48  | OH | 2 | 0 | —           | H            | 3         | CH$_3$ | SO$_2$CH$_2$CH$_2$OSO$_3$H (4) |
| 49  | OH | 3 | 0 | —           | H            | 3         | CH$_3$ | SO$_2$CH$_2$CH$_2$OSO$_3$H (4) |
| 50  | OH | 2 | 0 | —           | H            | 3         | COOH  | SO$_2$CH$_2$CH$_2$OSO$_3$H (3) |
| 51  | OH | 2 | 0 | —           | SO$_3$H (4)  | 3         | CH$_3$ | SO$_2$CH$_2$CH$_2$OSO$_3$H (4) |
| 52  | OH | 2 | 0 | —           | SO$_3$H (6)  | 3         | CH$_3$ | SO$_2$CH$_2$CH$_2$OSO$_3$H (4) |
| 53  | OH | 2 | 0 | —           | SO$_3$H (3)  | 4         | COOH  | SO$_2$CH=CH$_2$ (4) |
| 54  | OH | 2 | 1 | NH$_2$      | SO$_3$H (4)  | 3         | COOH  | SO$_2$CH$_2$CH$_2$OSO$_3$H (3) |
| 55  | OH | 2 | 1 | NH$_2$      | SO$_3$H (4)  | 3         | CH$_3$ | SO$_2$CH$_2$CH$_2$OSO$_3$H (4) |
| 56  | OH | 2 | 1 | NHCH$_2$CH$_2$OH | H       | 3         | COOH  | SO$_2$CH=CH$_2$ (4) |
| 57  | OH | 2 | 1 | NHCH$_2$CH$_2$SO$_3$H | H  | 3         | CH$_3$ | SO$_2$CH$_2$CH$_2$OSO$_3$H (3) |
| 58  | OH | 2 | 1 |             | H            | 3         | COOH  | SO$_2$CH$_2$CH$_2$OSO$_3$H (4) |

EXAMPLE 59

97 parts of the amino dyestuff of Example 45a was mixed with 600 parts of ice water and 18.4 parts of 2,4,6-trichlorotriazine were added with good stirring. The pH was adjusted to 6–6.5 over 3 hours with 20% sodium hydroxide. To this mixture was added a solution of (3'-aminobenzolsulphonyl)-2-sulphatoethane in 100 parts of water and the resulatant mixture was stirred for 4 hours whilst being maintained at a pH of 6–6.5 with a 15% sodium bicarbonate solution. After salting the product out of solution with sodium chloride, filtering and drying a compound 59 was obtained.

was stirred for 3 hours and was maintained at a pH of 5 to 6 with 20% sodium hydroxide. A solution of 17.2 parts of (2'-aminoethane-1'-sulphonyl)-2-chloroethane in 100 parts of ice water was added to the reaction mixture. The resultant mixture was stirred for 4 hours and the pH maintained at 6.5 to 7 with 20% sodium hydroxide. After salting the product out of solution using sodium chloride, filtering and drying, the product 60 was obtained.

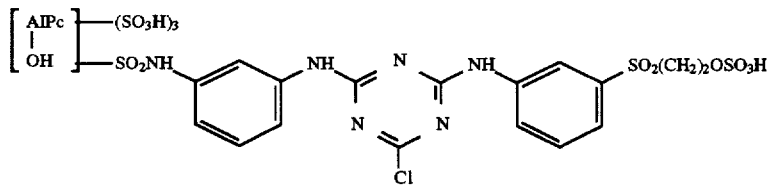

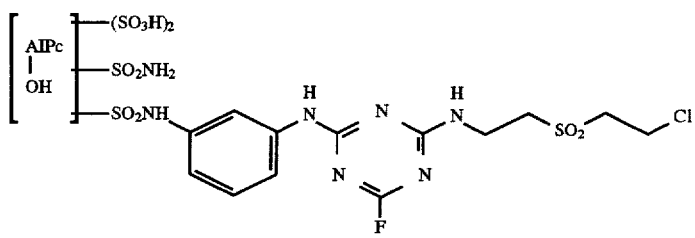

60

EXAMPLE 61

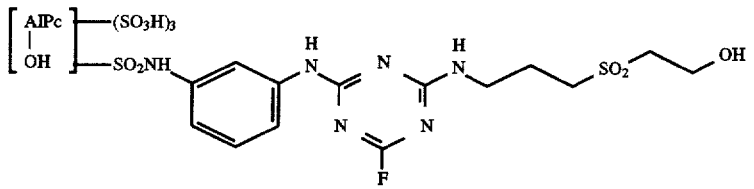

61a 97 parts of the amino dyestuff 45a was mixed in 600 parts of ice water and 13.5 parts of 2,4,6-trifluorotriazine were added at a temperature of from −5° to −10° C. The solution was stirred for 3 hours and was maintained at a pH of 5 to 6 with 20% sodium hydroxide. A solution of 16.7 parts of (2'-aminopropane-1'-sulphonyl)-ethane-2-ol in 100 parts of ice water was added to the reaction mixture. The resultant mixture was stirred for 4 hours and the pH maintained at 6.5 to 7 with 20% sodium hydroxide. After salting the product out of solution using sodium chloride, filtering and drying, the product 61a was obtained. This intermediate was converted to its sulphuric acid half ester as described in Example 3b.

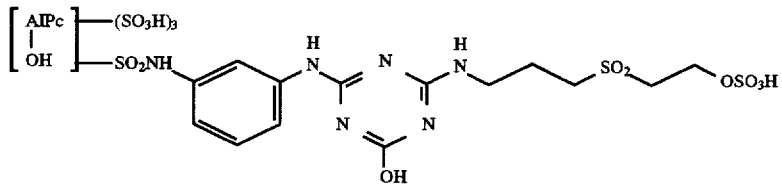

61b

EXAMPLES 62–73

The following fibre-reactive dyestuffs were obtained following the method of Examples 59 to 61.

TABLE 4

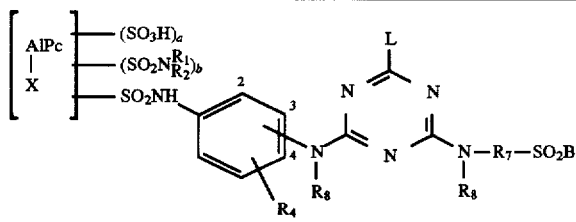

| Ex. | X | a | b | $NR_1R_2$ | $R_4$ (Pos.) | $NR_8$ (Pos.) | L | $NR_7R_8$ | $SO_2B$ |
|---|---|---|---|---|---|---|---|---|---|
| 62 | OH | 3 | 0 | — | H | NH(3) | F | $NHCH_2CH_2CH_2$ | $SO_2CH_2CH_2OSO_3H$ |
| 63 | OH | 3 | 0 | — | H | NH(3) | F | $NHCH=CH_2$ | $SO_2CH=CH_2$ |

TABLE 4-continued

| Ex. | X | a | b | NR₁R₂ | R₄ (Pos.) | NR₈ (Pos.) | L | NR₇R₈ | SO₂B |
|---|---|---|---|---|---|---|---|---|---|
| 64 | OH | 3 | 0 | — | SO₃H(4) | NH(3) | Cl | HN-C₆H₄- | SO₂CH₂CH₂OSO₃H |
| 65 | OH | 3 | 0 | — | SO₃H(6) | NH(3) | Cl | HN-C₆H₄- | SO₂CH₂CH₂OSO₃H |
| 66 | OH | 3 | 0 | — | SO₃H(6) | NH(3) | F | HN-C₆H₄- | SO₂CH=CH₂ |
| 67 | OH | 3 | 0 | — | SO₃H(3) | NH(3) | OH | HN-C₆H₄- | SO₂CH₂CH₂OSO₃H |
| 68 | OH | 3 | 0 | — | SO₃H(6) | NH(3) | F | NHCH₂CH₂OCH₂CH₂ | SO₂CH=CH₂ |
| 69 | OH | 3 | 0 | — | SO₃H(6) | NH(3) | OH | NHCH₂CH₂OCH₂CH₂ | SO₂CH₂CH₂OSO₃H |
| 70 | OH | 2 | 1 | NH₂ | SO₃H(4) | NH(3) | Cl | HN-C₆H₄- | SO₂CH₂CH₂OSO₃H |
| 71 | OH | 2 | 1 | NHCH₂CH₂OH | H | NH(3) | Cl | HN-C₆H₄- | SO₂CH=CH₂ |
| 72 | OH | 2 | 1 | NHCH₂CH₂SO₃H | H | NH(3) | F | HN-C₆H₄- | SO₂CH₂CH₂OSO₃H |
| 73 | OH | 2 | 1 | morpholino | H | NH(3) | F | HN-C₆H₄- | SO₂CH₂CH₂OSO₃H |

EXAMPLES 74

20 parts of PcAlCl. 2H₂O are stirred in 140 parts of chlorosulphonic acid for 30 minutes at 20° to 25° C. The reaction mixture is then heated to 135° to 140° C. over 2 hours. After 4 hours the reaction mixture is cooled to room temperature using an ice bath. The suspension thus formed is filtered and washed in ice water to remove excess acid.

97 parts of the product formed by the above reaction was stirred in 300 parts of water and 100 parts of ice. Thereafter, a solution of (3'-aminobenzosulphonyl)-2-sulphatoethane in 100 parts of ice water is added (3 moles per 1 mole of phthalocyanine). The pH of the resultant solution which is 1–2 is increased to 4–5 with 20% sodium hydroxide and thereafter left for 15 hours at a temperature of from 0° to 5° C. The resulant dyestuff is salted out with sodium chloride, filtered and dried at a temperature of from 40° to 50° C.

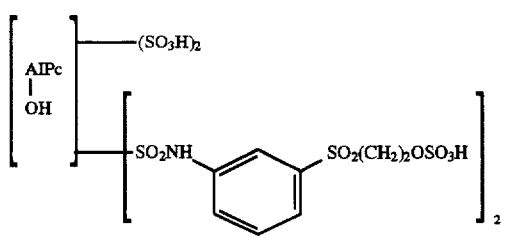

EXAMPLE 75

97 parts of the chlorosulphonated phthalocyanine obtained according to the methodology of Example 74 is stirred in 300 parts of water and 100 parts of ice. Thereafter, a solution of 14.5 parts of 1,3-diaminobenzene monohydrochloride in 100 parts of ice water is added under stirring. The pH of the resultant solution which is 1–2 is increased to 4–5 with 20% sodium hydroxide before adding 28.1 parts of (3'-aminobenzosulphonyl)-2-sulphatoethane and reacting for 15 hours at a temperature of from 0° to 5° C. to yield compound 75a.

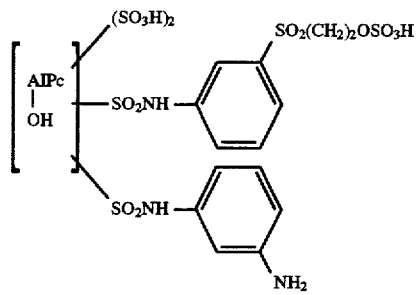

To the solution of 75a obtained according to the above procedure is added 14 parts of 2,4,6-trifluoropyrimidine at a pH of 5 to 6 (maintained with the addition of 15% sodium carbonate solution). The resultant dyestuff is salted out with sodium chloride, filtered and dried under vacuum at 40° to 50° C. The resultant dyestuff according to the formula 75 dyed cotton in brilliant green shades with good fastness properties.

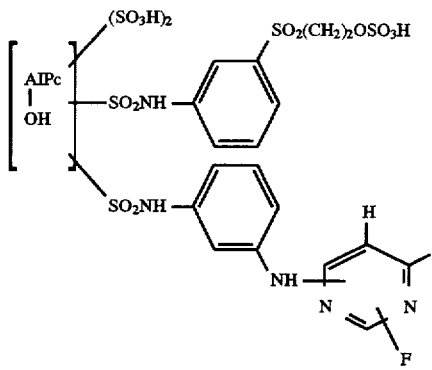

EXAMPLES 76 to 88

The compounds of Table 5 were formed according to a process analogous to the process described in Example 75. All compounds dyed cotton in brilliant green shades and displayed good fastness properties.

TABLE 5

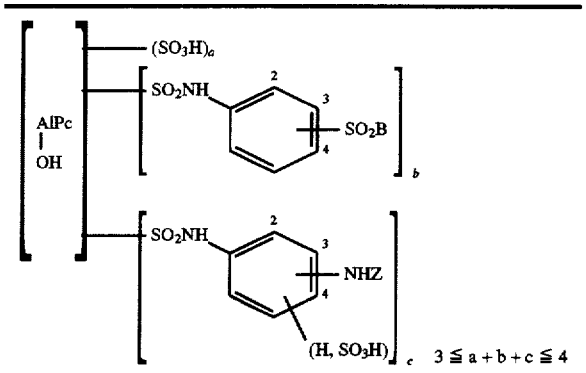

| Ex | a | $SO_2B$(Pos.) | H, $SO_3H$ | NHZ(Pos.) |
|---|---|---|---|---|
| 75 | 2 | $SO_2CH_2CH_2OSO_3H$(3) | H | $NHZ_3$(3) |
| 76 | 1 | $SO_2CH_2CH_2OSO_3H$(4) | H | $NHZ_3$(3) |
| 77 | 2 | $SO_2CH_2CH_2OSO_3H$(4) | H | $NHZ_4$(3) |
| 78 | 1 | $SO_2CH_2CH_2OSO_3H$(3) | $SO_3H$(4) | $NHZ_3$(3) |
| 79 | 1 | $SO_2CH_2CH_2OSO_3H$(3) | $SO_3H$(4) | $NHZ_4$(3) |
| 80 | 1.5 | $SO_2CH_2CH_2OSO_3H$(3) | H | $NHZ_3$(3) |
| 81 | 1 | $SO_2CH_2CH_2OSO_3H$(3) | $SO_3H$(4) | $NHZ_4$(3) |
| 82 | 1.5 | $SO_2CH_2CH_2OSO_3H$(3) | $SO_3H$(4) | $NHZ_4$(3) |
| 83 | 2 | $SO_2CH=CH_2$(4) | $SO_3H$(4) | $NHZ_4$(3) |
| 84 | 2 | $SO_2CH_2CH_2OSO_3H$(3) | $SO_3H$(4) | $NHZ_5$(3) |
| 85 | 2 | $SO_2CH=CH_2$(3) | H | $NHZ_3$(3) |
| 86 | 2 | $SO_2CH=CH_2$(3) | H | $NHZ_4$(3) |
| 87 | 1.5 | $SO_2CH=CH_2$(3) | $SO_3H$(3) | $NHZ_5$(4) |
| 88 | 1 | $SO_2CH_2CH_2OSO_3H$(4) | $SO_3H$(3) | $NHZ_5$(4) |

EXAMPLE 89

The process of Example 75 is followed. However, rather than adding 2,4,6-trifluoropyrimidine to the solution of compound 75a, 13.5 parts of 2,4,6-trifluorotriazine is added and the condensation reaction is carried out at 0°–10° C. and at a pH of 4 to 5 (using 15% sodium carbonate solution). 9 parts of morpholine is added to the resultant condensation product at a pH of 5 to 16 and a temperature of 0° to 25° C. The resultant dyestuff having the formula 89 is salted out using sodium chloride, filtered and dried under vacuum at 40° to 50° C.

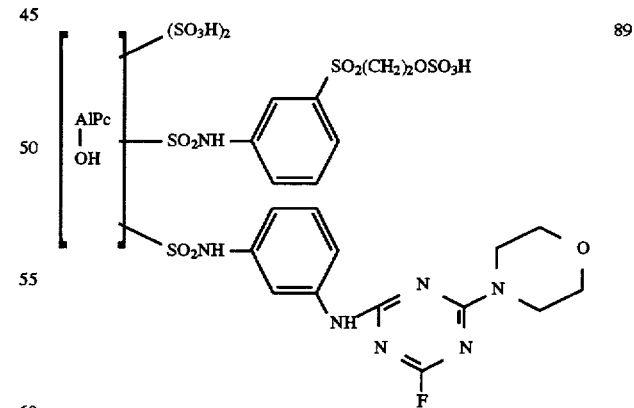

EXAMPLES 90 to 92

The compounds of Table 6 were formed according a process analogous to that of Example 89. All compounds dye cotton to brilliant green shades and displayed good fastness properties.

TABLE 6

$$\left[ AlPc(OH) \begin{array}{l} -(SO_3H)_a \\ -SO_2NH-An-SO_2B]_b \\ -SO_2NH-\underset{(H, SO_3H)}{\underset{4}{\bigcirc}}\overset{2}{\underset{3}{-}}NHZ \end{array} \right]_c \quad 3 \leq a+b+c \leq 4$$

| Ex | a | −SO₂B | Aₙ | H, SO₃H | −NHZ |
|---|---|---|---|---|---|
| 90 | 1 | −SO₂(CH₂)₂OSO₃H(3) | (phenyl, 3-methyl) | SO₃H (4) | −NHZ₈(3) |
| 91 | 1 | −SO₂CH=CH₂ | (CH₂)₂O(CH₂)₂ | H | −NHZ₇(3) |
| 92 | 1 | −SO₂CH=CH₂ | (CH₂)₂O(CH₂)₂ | H | −NHZ₇(3) |

The compounds of Table 7 were formed according to a process analogous to the process described in Example 75. All compounds dye cotton to brilliant green shades.

TABLE 7

$$\left[ AlPc(OH) \begin{array}{l} -(SO_3H)_a \\ -SO_2NH-An-SO_2B]_b \\ -SO_2NH-\underset{(H, SO_3H)}{\underset{4}{\bigcirc}}\overset{2}{\underset{3}{-}}NHZ \end{array} \right]_c \quad 3 \leq a+b+c \leq 4$$

| Ex.- | a | Aₙ | SO₂B | H, SO₃H | NHZ (Pos.) |
|---|---|---|---|---|---|
| 93 | 1 | CH₂CH₂ | CH=CH₂ | SO₃H(4) | NHZ₃(3) |
| 94 | 1 | CH₂CH₂CH₂ | CH=CH₂ | H | NHZ₃(3) |

TABLE 7-continued $$\left[ AlPc(OH) \begin{array}{l} -(SO_3H)_a \\ -SO_2NH-An-SO_2B]_b \\ -SO_2NH-\underset{(H, SO_3H)}{\underset{4}{\bigcirc}}\overset{2}{\underset{3}{-}}NHZ \end{array} \right]_c \quad 3 \leq a+b+c \leq 4$$

| Ex.- | a | Aₙ | SO₂B | H, SO₃H | NHZ (Pos.) |
|---|---|---|---|---|---|
| 95 | 1.5 | CH₂CH₂ | CH=CH₂ | H | NHZ₄(3) |
| 96 | 2 | CH₂CH₂OCH₂CH₂ | CH₂CH₂Cl | H | NHZ₃(3) |
| 97 | 1.5 | CH₂CH₂CH₂ | CH₂CH₂Cl | SO₃H(4) | NHZ₅(3) |
| 98 | 2 | CH₂CH₂OCH₂CH₂ | CH=CH₂ | H | NHZ₃(3) |
| 99 | 1 | CH₂CH₂CH₂ | CH=CH₂ | SO₃H(4) | NHZ₄(3) |
| 100 | 1.5 | CH₂CH₂CH₂ | CH=CH₂ | H | NHZ₅(3) |

EXAMPLE 101

A compound corresponding to Example 75a is diazotised according to the procedure of Example 16 in German Patent DOS 1 9521056. The diazonium salt suspension was poured onto a solution of 300 parts of ice water and 20 parts of 1-(3'-methylaminopropyl)-6-hydroxy-4-methylpyridone-(2) at 0° to 5° C. The pH is maintained at 6.5 to 7.5 with additions of 15% sodium carbonate solution. 24 parts of 5-cyano-2,4,6-trichloropyrimidine are added to the resultant reaction mixture at 20° to 30° C. whilst maintaining the pH at a constant 7.5–8 with additions of 15% sodium carbonate solution. The resultant dyestuff is salted out using sodium chloride, filtered and dried under vacuum at 40° to 50° C. to yieled the dyestuff having the formula 101

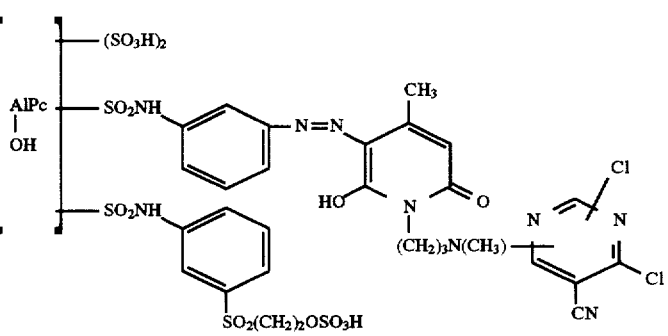

EXAMPLES 102 to 105

The compounds in Table 8 are formed by a process analogous to that described in Example 101. All compounds dye cotton to green shades and displayed good fastness properties.

TABLE 8

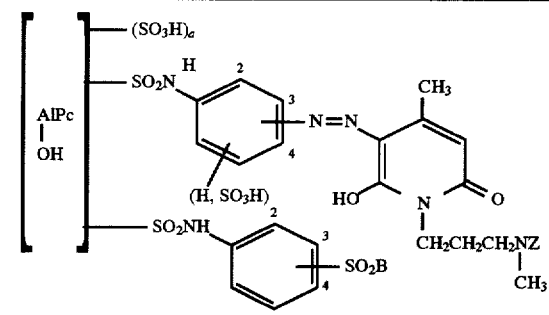

$$3 \leq a+b+c \leq 4$$

| Ex. | a | H, SO₃H | Z | —N=N(Pos.) | SO₂B(Pos.) |
|---|---|---|---|---|---|
| 102 | 1 | SO₃H(4) | Z₅ | 3 | SO₂CH₂CH₂OSO₃H(4) |
| 103 | 1.5 | SO₃H(4) | Z₅ | 3 | SO₂CH₂CH₂OSO₃H(3) |
| 104 | 2 | SO₃H(4) | Z₅ | 3 | SO₂CHCH₂(4) |
| 105 | 2 | SO₃H(4) | Z₅ | 3 | SO₂CHCH₂(5) |

EXAMPLE 106 to 110

The compounds of Table 9 were formed according to a process analogous to the process described in Example 101. All compounds dye cotton to green shades and displayed good fastness properties.

EXAMPLE 111

The process according to Example 75 is followed with the modification that instead of using 28.1 parts of 3'-aminobenzenesulphonyl)-2-sulphoethane one uses 50 parts of a compound according to the formula 111 a

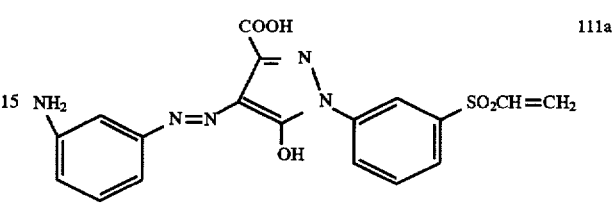

Therafter, 14 parts of 2,4,6-trifluoropyrimidine are added to the reaction mixture whilst maintaining the pH constant at 5 to 6 with additions of 15% sodium carbonate solution. The resultant product was salted out with sodium chloride, filtered and dried in a vacuum at 40 to 50° C. to yield the dyestuff of the formula 111 which dyes cotton to brilliant green shades and has good fastness properties.

TABLE 9

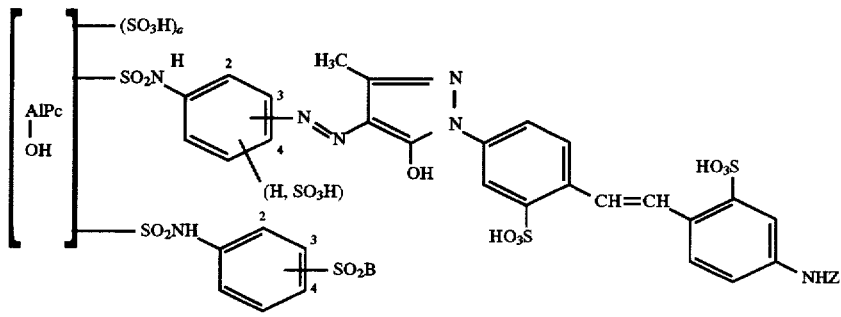

| Ex. | a | H, SO₃H) | Z | —N=N(Pos.) | SO₂B(Pos.) |
|---|---|---|---|---|---|
| 106 | 1 | SO₃H(4) | Z₉ | 3 | SO₂CH₂CH₂OSO₃H(3) |
| 107 | 1 | SO₃H(4) | Z₉ | 3 | SO₂CH₂CH₂OSO₃H(4) |
| 108 | 1.5 | SO₃H(4) | Z₉ | 3 | SO₂CH₂CH₂OSO₃H(3) |
| 109 | 1.5 | SO₃H(4) | Z₉ | 3 | SO₂CH₂CH₂OSO₃H(4) |
| 110 | 2 | SO₃H(4) | Z₅ | 3 | SO₂CH₂CH₂OSO₃H(4) |

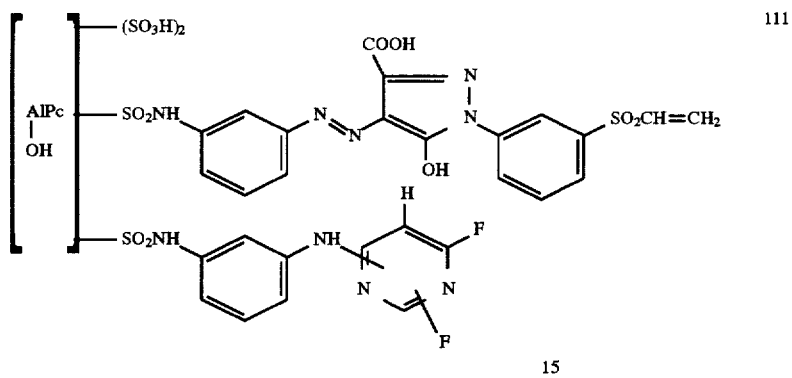

111

EXAMPLES 112 to 116

The compounds of Table 10 were formed according to a process analogous to the process described in Example 111. All the compounds dye cotton to brilliant green shades.

TABLE 10

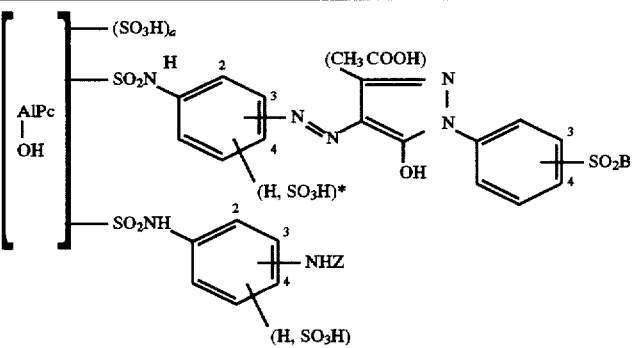

| Ex. | a | (H, SO₃H)* | CH₃, COOH | SO₃B (Pos.) | H, SO₃H (Pos.) | NHZ (Pos.) |
|---|---|---|---|---|---|---|
| 112 | 1   | SO₃H(4) | CH₃  | CH₂CH₂OSO₃H(4) | H       | NHZ₃(3) |
| 113 | 1.5 | SO₃H(4) | COOH | CH=CH₂(4)      | H       | NHZ₄(3) |
| 114 | 2   | H       | CH₃  | CH₂CH₂OSO₃H(3) | H       | NHZ₃(3) |
| 115 | 1.5 | H       | COOH | CH₂CH₂OSO₃H(4) | SO₃H(4) | NHZ₅(3) |
| 116 | 2   | SO₃H(4) | CH₃  | CH₂CH₂OSO₃H    | SO₄H(4) | NHZ₃(3) |

TABLE 11

UV absorbances measured in water (λmax/nm)

| Ex. | λmax | Ex. | λmax |
|---|---|---|---|
| 1  | 672 | 20 | 663 |
| 2  | 675 | 21 | 668 |
| 3  | 668 | 22 | 670 |
| 4  | 667 | 23 | 667 |
| 5  | 671 | 24 | 666 |
| 6  | 669 | 25 | 672 |
| 7  | 670 | 26 | 672 |
| 8  | 670 | 27 | 660 |
| 9  | 665 | 28 | 670 |
| 10 | 668 | 29 | 671 |
| 11 | 664 | 30 | 673 |
| 12 | 667 | 31 | 674 |
| 13 | 668 | 32 | 668 |
| 14 | 671 | 33 | 667 |
| 15 | 669 | 34 | 669 |
| 16 | 670 | 35 | 670 |
| 17 | 665 | 36 | 665 |
| 18 | 666 | 37 | 671 |
| 19 | 668 | 38 | 670 |

TABLE 11-continued

UV absorbances measured in water (λmax/nm)

| Ex. | λmax |
|---|---|
| 39 | 665 |
| 40 | 672 |
| 41 | 673 |
| 42 | 664 |
| 43 | 669 |
| 44 | 674 |
| 45 | 671 |
| 46 | 664 |
| 47 | 669 |
| 48 | 672 |
| 49 | 670 |
| 50 | 665 |
| 51 | 676 |
| 52 | 664 |
| 53 | 671 |
| 54 | 668 |
| 55 | 664 |
| 56 | 667 |
| 57 | 667 |
| 58 | 665 |
| 59 | 671 |
| 60 | 669 |
| 61 | 670 |
| 62 | 674 |
| 63 | 675 |
| 64 | 666 |
| 65 | 672 |
| 66 | 670 |
| 67 | 671 |
| 68 | 661 |
| 69 | 673 |
| 70 | 671 |
| 71 | 665 |
| 72 | 672 |
| 73 | 671 |
| 74 | 667 |
| 75 | 669 |
| 76 | 665 |
| 77 | 675 |
| 78 | 674 |
| 79 | 667 |
| 80 | 668 |
| 81 | 672 |
| 82 | 665 |
| 83 | 668 |
| 84 | 663 |
| 85 | 669 |
| 86 | 673 |
| 87 | 666 |
| 88 | 668 |
| 89 | 672 |
| 90 | 667 |
| 91 | 665 |
| 92 | 668 |
| 93 | 673 |
| 94 | 665 |
| 95 | 667 |
| 96 | 675 |
| 97 | 673 |
| 98 | 670 |
| 99 | 670 |
| 100 | 669 |
| 101 | 663 |
| 102 | 665 |
| 103 | 666 |
| 104 | 672 |
| 105 | 669 |
| 106 | 672 |
| 107 | 667 |
| 108 | 670 |
| 109 | 668 |
| 110 | 667 |
| 111 | 671 |
| 112 | 668 |
| 113 | 666 |
| 114 | 672 |
| 115 | 664 |
| 116 | 668 |

Application Example A

To a dye bath consisting of 100 g of demineralized water, 0.25 g of the dyestuff of Example 1 and 10 g of cotton tricot (bleached) are added. The dyebath is heated to 50° C. over a 10 minutes period and maintained at this temperature for 25 minutes. Thereafter, 0.4 g of calcinated sodium carbonate and 0.3 ml of concentrated caustic soda-solution are added. After 30 minutes at 50° C. the temperature is increased to 60° C. over a 25 minutes period and dyeing is continued for 60 minutes at this temperature. The dyed cotton fabric is removed from the liquor, rinsed for 10 minutes in 500 g of demineralized water in the presence of 0.25 g of a non-ionic surfactant. Finally the cotton dyeing is rinsed and dried. The green dyeing obtained displays good all-round fastness.

The Example is repeated with the compound of Example 74. The green dyeing obtained displays good all round fastness properties.

Application Example B

A printing paste having the components
40 parts of the dyestuff of the Example 1
100 parts of urea
350 parts of water
500 parts of a 4% sodium alginate thickener
10 parts of sodium bicarbonate 1000 parts in all was applied to cotton material by a conventional printing process.

The printed and dried material was steamed for 4 to 8 minutes at 102° to 105° C. and then given a cold and hot rinse. The fixed cotton material was then washed twice for 10 minutes, each time in 5000 parts of boiling, demineralised water, subsequently rinsed for 2 minutes in running, demineralised water of 60° C.±10° C., 1 minute in running tap water of 60° C. ±10° C. and for 1 minute in cold tap water.

The Example was repeated for the compound of Example 74.

We claim:

1. Compounds of formula (I)

$$\left[ MPc \begin{array}{l} -(SO_3H)_a \\ -(SO_2NR_1R_2)_b \\ -(SO_2NR_a-RG)_c \end{array} \right]$$

and their salts
wherein, $R_1$ is hydrogen, or an open chain hydrocarbon group having from 1 to 8 carbon atoms or an open chain hydrocarbon group having 1 to 8 carbon atoms comprising oxygen, nitrogen or sulphur atoms, $R_2$ is, independently of $R_1$, any of the significances of $R_1$ or is a group —$A_nSO_2$—B or —$A_nSO_2$—B' wherein B is selected from ant of the groups according to the formula —CH=CH$_2$, —CH$_2$CH—Y, —CH=CH—Y or —CH(CH$_2$Y)—CH$_2$Y wherein Y represents a hydroxyl group or a group selected from halogen, —OSO$_3$H or —SO$_3$H, —OPO$_2$H$_2$, —SSO$_3$H, —OCOCH$_3$, —OCOC$_5$H$_5$, —OCO(CH$_2$)$_2$

—COOH, —OCO—CH=CH—COOH, —OCO—C6H4—COOH, OCO—COOH,

—OSO$_2$CH$_3$, a quaternary nitrogen group, or bivalent groups —OCO—COO—,

—OCO—(CH$_2$)$_2$—COO—, —OCO—CH=CH—COO and OCO—C$_6$H$_4$—COO—, or R1 and R2 taken together form a 3 to 6 carbon heterocyclic ring also comprising Nitrogen and optionally oxygen; B' is —(CH$_2$)$_2$—OSO$_3$H and $A_n$ is $A_1$ to $A_3$ wherein
$A_1$ is a group

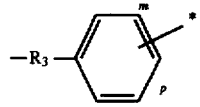

wherein * is a bond connected to SO$_2$B
and R$_3$ is a direct bond or is —(CH$_2$)$_2$—, A$_2$ is a group A1 in which R$_3$ is a direct bond or is an alkylene or oxyalkylene group having from 2 to 4 carbon atoms, and A$_3$ is a group represented by the formula

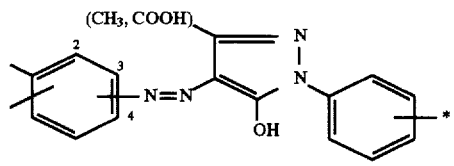

(wherein * is a bond connected to SO$_2$B)

R$_1$ and R$_2$ together represent a divalent alkylene or aralkylene group, or a divalent alkylene or aralkylene group bearing oxygen, nitrogen or sulphur atoms, R$_a$ is hydrogen, alkyl having 1 to 4 carbon atoms, hydroxyalkyl having 2 to 4 carbon atoms or a group —A$_x$SO$_2$—B wherein B is as hereinabove defined and A$_x$ is defined below.

RG is a group containing a fibre-reactive group and is selected from —A$_x$SO$_2$—B or —D—NR$_{10}$Z wherein A$_x$ is represented by a divalent hydrocarbon group or a divalent hydrocarbon group comprising oxygen, nitrogen or sulphur atoms; or an aza-alkylene group —(CH$_2$)$_2$—NR$_4$—(CH$_2$)$_2$— wherein R$_4$ is a C$_{1-4}$ alkyl group or a C$_{1-4}$ alkyl group substituted with a hydroxyl group; an arylene group

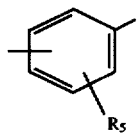

wherein R$_5$ represents a hydrogen atom, halogen atom, an alkyl group having 1 to 4 carbon atoms, an alkoxy group having 1 to 4 carbon atoms, —SO$_3$H or —COOH; phenylene azophenylpyrazolaryl group according to the formula

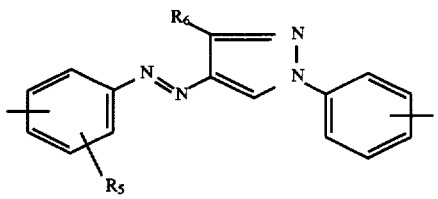

wherein R$_5$ is as hereinbefore defined and R6 is a methyl group or a group —COOH; or a triazine group according to the formula

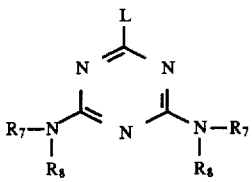

wherein L is a hydroxyl group, a halogen atom, or an amino group NR$_1$R'$_2$ wherein R$_2$ is any of the significances of R$_1$ or together with R$_1$ is a divalent alkylene or aralkylene group or a divalent alkylene or aralkylene group bearing an oxygen, nitrogen or sulphur atom, or a pyridinium group

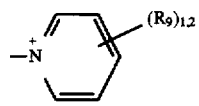

wherein R$_9$ is —SO$_3$H or —COOH,

R$_7$ is a divalent group selected from alkylene, oxaalkylene, arylene or aralkylene, R$_8$ is a hydrogen atom, an alkyl group having 1 to 4 carbon atoms, or a hydroxyalkyl group having 2 to 4 carbon atoms, Z represents a heterocyclic fibre-reactive radical selected from halo-triazine or halo-pyrimidine having a labile fluorine or chlorine atom R$_{10}$ is H or Ch3 and D represents a divalent residue selected from

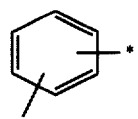    D1

(H, So$_3$H)  (wherein * represents a bond to NR$_{10}$Z)

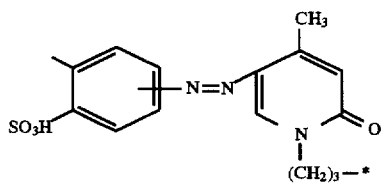    D2

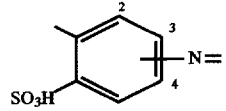    D3

M is AlOH or AlCl

Pc is a phthalocyanine radical a is 1, 2 or 3 b is 0, 1, 2 or 3 c is 0, 1 or 2 and a+b+c has a value which is greater than or equal to 3 and less than or equal to 4 and b and c cannot be zero at the same time, with the provisos that, i) when c is 1 or 2, RG is —D—NR$_{10}$Z and D is D$_1$, then b is 1 or 2, R$_2$ is —A2SO$_2$— B and R$_a$ is not A$_x$SO$_2$—B ii) when c is 1, RG is —D—NR$_{10}$Z and D is D$_2$ or D$_3$, then be is 1 or 2, R$_2$ is —A$_2$SO$_2$— B and R$_a$ is not A$_x$SO$_2$—B, iii) when c is 1, RG is —D—NR$_{10}$Z and D is D$_1$ then b is 1, R$_2$ is —A$_3$SO$_2$— B and R$_a$ is not A$_x$SO$_2$—B, iv) when c is 1 and RG is A$_x$SO$_2$—B, then R$_2$ is independently of R$_1$, any of the significances of R$_1$, and v) when c is zero, then b is 1 or 2, R$_2$ is A$_1$SO$_2$—B'.

2. Compounds according to claim 1 and their salts wherein the group Z is selected from the fiber-reactive radicals Z$_1$ to Z$_9$ defined hereinbelow 3. Compounds according to claim 1 or claim 2 having the formula (Ia)

$$\left[ MPc \right] \begin{matrix} -(SO_3H)_a \\ -(SO_2NR_1R_2)_b \\ -(SO_2NR_a-A_x-SO_2-B) \end{matrix} \quad (Ia)$$

and their salts wherein A$_x$, M, Pc, R$_a$, R$_1$ and R$_2$ together and B are as defined in claim 1, R$_1$ and R$_2$ are independently hydrogen, a hydrocarbon group having from 1 to 8 carbon atoms or a hydrocarbon group having from 1 to 8 carbon atoms comprising oxygen, nitrogen or sulphur atoms, and a has a value of 1, 2 or 3 and b has a value of 0, 1 or 2 provided that a+b is not greater than 3.

4. Compounds according to claim 2 of the formula (Ib)

$$\left[ MPc \right] \begin{matrix} -(SO_3H)_a \\ -(SO_2NR_1-A_1-SO_2-B')_b \end{matrix}$$

and their salts, wherein

Pc, A$_1$, M and B' are as defined in claim 1 and a is 1, 2 or 3, b is 1, 2 or 3 and a+b is a value of 3 or 4.

5. Compounds according to claim 4 having the formula (Ib)

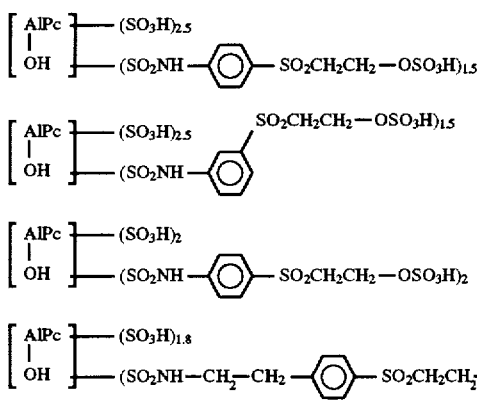

and their salts.

6. Compounds according to claim 2 having the formula (Ic)

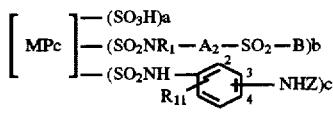

and their salts wherein the symbols Pc, M, Z, A$_2$, R$_1$, B and a are as defined in claim 1 or claim 2, R$_{11}$ is hydrogen or —SO$_3$H, c is 1 or 2 and b is 1 or 2, provided that a+b+c is 3 or 4.

7. Compounds according to claim 6 their salts and mixtures thereof wherein A$_2$ is represented by phenylene, —(CH$_2$)$_n$—, wherein n is 2 or 3 or —(CH$_2$)$_2$—O—(CH$_2$)$_2$—.

8. Compounds according to claim 6 their salts and mixtures thereof wherein B is represented by —CH$_2$CH$_2$OSO$_3$H, CH$_2$CH$_2$Cl or —CH=CH$_2$.

9. Compounds according to claim 6, their salts and mixtures thereof wherein A$_2$ is phenylene when B is —CH$_2$CH$_2$OSO$_3$H and A$_2$ is —(CH$_2$)$_n$—, wherein n is 2 or 3 or —(CH$_2$)$_2$—O—(CH$_2$)$_2$— when B is —CH$_2$CH$_2$Cl or —CH=CH$_2$.

10. Compounds according to claim 1 having the formula (Id)

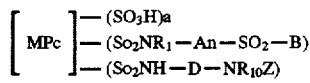

and their salts, wherein the symbols D, Z, B, Pc, M, A$_n$, R$_{10}$ are as described in claim 1 and a has a value of 1 or 2.

11. Compounds according to claim 10, and their salts wherein the group A$_n$ is A$_1$, D is D$_2$, B is —CH$_2$CH$_2$OSO$_3$H or —CH=CH$_2$ and Z is Z$_5$; A$_n$ is A$_1$, D is D$_3$, B is —CH$_2$CH$_2$OSO$_3$H and Z is Z$_5$ or Z$_9$; and A$_n$ is A$_3$, D is D$_1$, B is —CH$_2$CH$_2$OSO$_3$H or —CH=CH$_2$ and Z is Z$_3$, Z$_4$ or Z$_5$.

12. Compounds of the following formulas:

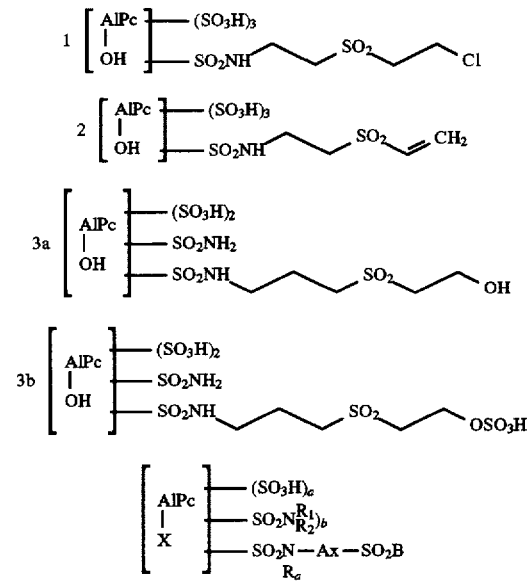

| Ex. | X  | a | b | NR$_1$R$_2$ | R$_a$           | A$_z$          | B             |
|-----|----|---|---|-------------|-----------------|----------------|---------------|
| 4   | OH | 2 | 1 | NH$_2$      | H               | CH$_2$CH$_2$   | CH=CH$_2$     |
| 5   | OH | 2 | 1 | NH$_2$      | H               | CH$_2$CH$_2$   | CH$_2$CH$_2$Cl|
| 6   | OH | 2 | 1 | NH$_2$      | H               | CH$_2$CH$_2$CH$_2$ | CH=CH$_2$ |
| 7   | OH | 2 | 1 | NH$_2$      | H               | CH$_2$CH$_2$OCH$_2$CH$_2$ | CH$_2$CH$_2$Cl |
| 8   | Cl | 2 | 1 | NH$_2$      | H               | CH$_2$CH$_2$OCH$_2$CH$_2$ | CH=CH$_2$ |
| 9   | OH | 2 | 1 | NH$_2$      | CH$_2$CH$_2$SO$_2$CH=CH$_2$ | CH$_2$CH$_2$ | CH=CH$_2$ |
| 10  | OH | 2 | 1 | NHCH$_3$    | H               | CH$_2$CH$_2$   | CH$_2$Cl      |

-continued

| | | | | | | | |
|---|---|---|---|---|---|---|---|
| 11 | OH | 2 | 1 | NH$_2$ | H | CH$_2$CH$_2$CH$_2$*<br>    |<br>CH$_2$CH<br>    |<br>SO$_2$CH$_2$CH$_2$Cl | CH$_2$CH$_2$Cl |
| 12 | OH | 2 | 1 | NH$_2$ | H | CH$_2$CH$_2$CH$_2$*<br>    |<br>CH$_2$CH<br>    |<br>SO$_2$CH=CH$_2$ | CH=CH$_2$ |
| 13 | OH | 2 | 1 | NHCH$_2$CH$_2$OH | H | CH$_2$CH$_2$ | CH=CH$_2$ |
| 14 | OH | 2 | 1 | NHCH$_2$CH$_2$OSO$_3$H | H | CH$_2$CH$_2$ | CH$_2$CH$_2$OSO$_3$H |
| 15 | OH | 2 | 1 | NHCH$_2$CH$_2$SO$_3$H | H | CH$_2$CH$_2$ | CH=CH$_2$ |
| 16 | OH | 2 | 1 | N(CH$_3$)CH$_2$CH$_2$SO$_3$H | H | CH$_2$CH$_2$ | CH=CH$_2$ |
| 17 | OH | 2 | 1 | | H | CH$_2$CH$_2$ | CH=CH$_2$ |
| 18 | OH | 2 | 1 | N(CH$_3$)CH$_2$CH$_2$OH | H | CH$_2$CH$_2$OCH$_2$CH$_2$ | CH=CH$_2$ |
| 19 | OH | 2 | 1 | NHCH$_2$CH$_2$CH$_2$OH | H | CH$_2$CH$_2$ | CH=CH$_2$ |
| 20 | OH | 2 | 0 | | H | CH$_2$CH$_2$OCH$_2$CH$_2$ | CH=CH$_2$ |
| 21 | OH | 2 | 0 | | H | CH$_2$CH$_2$ | CH=CH$_2$ |
| 22 | OH | 3 | 0 | | H | CH$_2$CH$_2$CH$_2$ | CH$_2$CH$_2$Cl |
| 23 | OH | 3 | 0 | | H | CH$_2$CH$_2$OCH$_2$CH$_2$ | CH$_2$CH$_2$Cl |

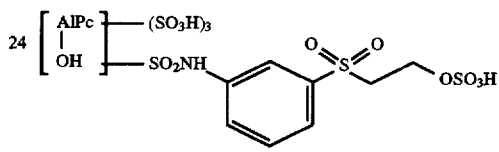

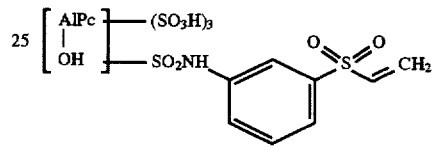

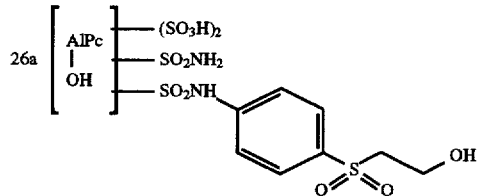

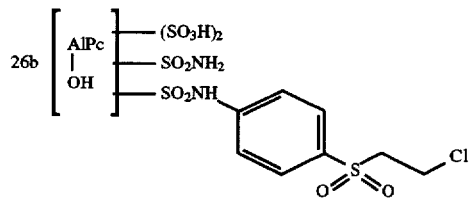

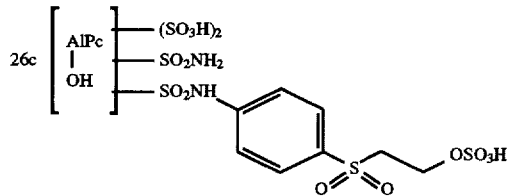

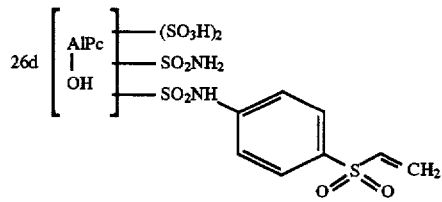

-continued

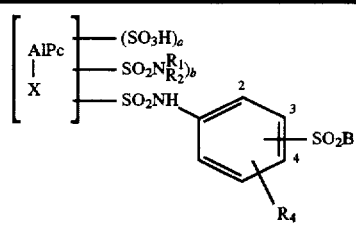

| Ex. | X | a | b | NR₁R₂ | R₄ (Pos.) | SO₂B (Pos.) |
|---|---|---|---|---|---|---|
| 27 | OH | 2 | 1 | NH₂ | H | SO₂CH₂CH₂OSO₃H (3) |
| 28 | OH | 2 | 1 | NH₂ | H | SO₂CH=CH₂ (3) |
| 29 | OH | 2 | 1 | NHCH₂CH₂OH | H | SO₂CH₂CH₂OSO₃H (4) |
| 30 | OH | 2 | 1 | NHCH₂CH₂OH | H | SO₂CH₂CH₂OSO₃H (3) |
| 31 | OH | 2 | 1 | NHCH₂CH₂SO₃H | H | SO₂CH₂CH₂OSO₃H (4) |
| 32 | OH | 2 | 1 | N(CH₃)CH₂CH₂SO₃H | H | SO₂CH₂CH₂OSO₃H (3) |
| 33 | OH | 2 | 1 | morpholino | H | SO₂CH=CH₂ (4) |
| 34 | OH | 2 | 1 | N(CH₃)CH₂CH₂OH | H | SO₂CH₂CH₂OSO₃H (4) |
| 35 | OH | 2 | 1 | N(CH₃)CH₂CH₂OH | H | SO₂CH₂CH₂OSO₃H (3) |
| 36 | OH | 2 | 1 | NHCH₂CH₂(OH)CH₃ | H | SO₂CH₂CH₂OSO₃H (4) |
| 37 | OH | 2 | 1 | NHCH₂CH₂CH₂OH | H | SO₂CH₂CH₂OSO₃H (4) |
| 38 | OH | 2 | 1 | NHCH₂CH₂CH₂OH | H | SO₂CH₂CH₂OSO₃H (3) |
| 39 | OH | 2 | 1 | NHCH₂CH₂COOH | H | SO₂CH₂CH₂OSO₃H (4) |
| 40 | OH | 1 | 0 | — | SO₃H (2) | SO₂CH₂CH₂OSO₃H (5) |
| 41 | OH | 1 | 0 | — | SO₃H (2) | SO₂CH₂CH₂OSO₃H (4) |
| 42 | OH | 2 | 0 | — | H | SO₂CH₂CH₂OSO₃H (3) |
| 43 | OH | 2 | 0 | — | H | SO₂CH₂CH₂OSO₃H (4) |
| 44 | OH | 3 | 0 | — | H | SO₂CH₂CH₂OSO₃H (4) |

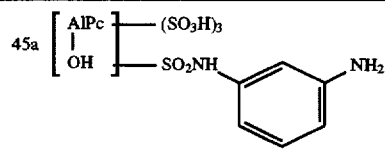

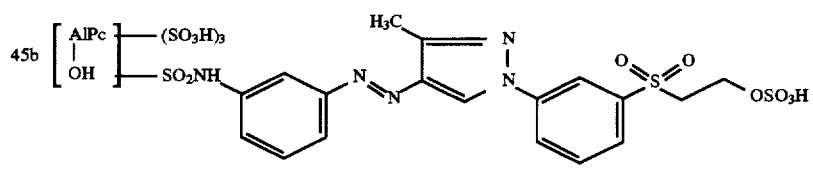

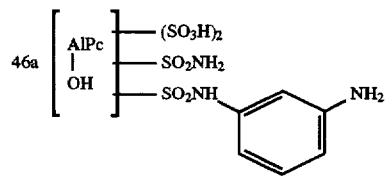

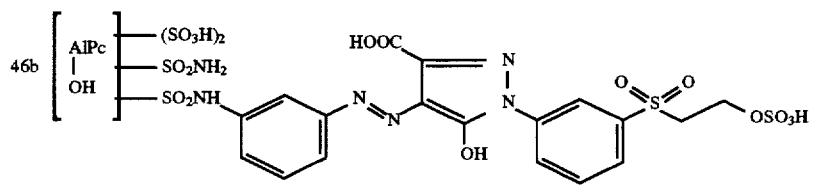

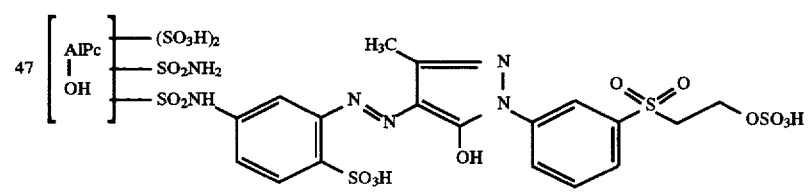

-continued

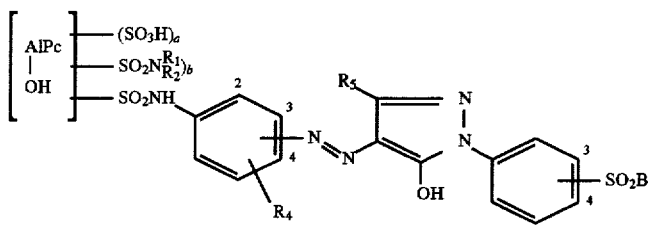

| Ex. | X | a | b | NR₁R₂ | R₄ (Pos.) | —N=N Pos. | R₅ | SO₂B (Pos.) |
|---|---|---|---|---|---|---|---|---|
| 48 | OH | 2 | 0 | — | H | 3 | $CH_3$ | $SO_2CH_2CH_2OSO_3H$ (4) |
| 49 | OH | 3 | 0 | — | H | 3 | $CH_3$ | $SO_2CH_2CH_2OSO_3H$ (4) |
| 50 | OH | 2 | 0 | — | H | 3 | COOH | $SO_2CH_2CH_2OSO_3H$ (3) |
| 51 | OH | 2 | 0 | — | $SO_3H$ (4) | 3 | $CH_3$ | $SO_2CH_2CH_2OSO_3H$ (4) |
| 52 | OH | 2 | 0 | — | $SO_3H$ (6) | 3 | $CH_3$ | $SO_2CH_2CH_2OSO_3H$ (4) |
| 53 | OH | 2 | 0 | — | $SO_3H$ (3) | 4 | COOH | $SO_2CH=CH_2$ (4) |
| 54 | OH | 2 | 1 | $NH_2$ | $SO_3H$ (4) | 3 | COOH | $SO_2CH_2CH_2OSO_3H$ (3) |
| 55 | OH | 2 | 1 | $NH_2$ | $SO_3H$ (4) | 3 | $CH_3$ | $SO_2CH_2CH_2OSO_3H$ (4) |
| 56 | OH | 2 | 1 | $NHCH_2CH_2OH$ | H | 3 | COOH | $SO_2CH=CH_2$ (4) |
| 57 | OH | 2 | 1 | $NHCH_2CH_2SO_3H$ | H | 3 | $CH_3$ | $SO_2CH_2CH_2OSO_3H$ (3) |
| 58 | OH | 2 | 1 | $NHCH_2CH_2SO_3H$ | H | 3 | COOH | $SO_2CH_2CH_2OSO_3H$ (4) |

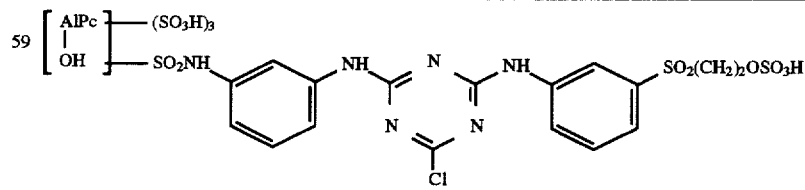

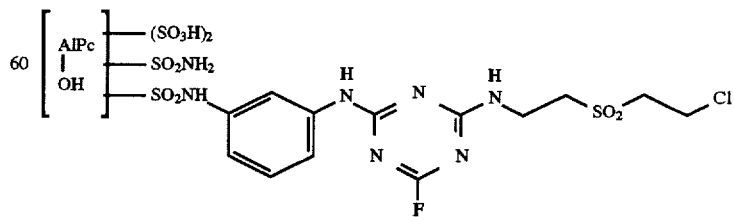

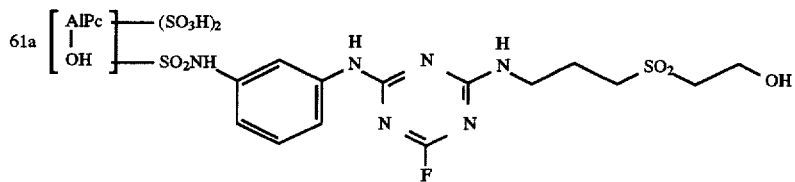

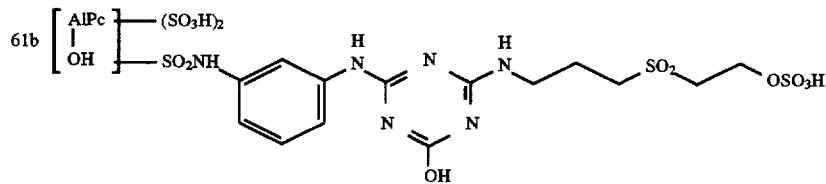

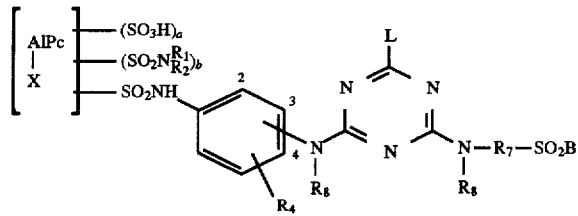

| Ex. | X | a | b | NR₁R₂ | R₄ (Pos.) | NR₇ (Pos.) | L | NR₇R₈ | SO₂B |
|---|---|---|---|---|---|---|---|---|---|
| 62 | OH | 3 | 0 | — | H | NH (3) | F | $NHCH_2CH_2CH_2$ | $SO_2CH_2CH_2OSO_3H$ |
| 63 | OH | 3 | 0 | — | H | NH (3) | F | $NHCH=CH_2$ | $SO_2CH=CH_2$ |

-continued

| | | | | | | | | | |
|---|---|---|---|---|---|---|---|---|---|
| 64 | OH | 3 | 0 | — | SO$_3$H (4) | NH (3) | Cl | " | SO$_2$CH$_2$CH$_2$OSO$_3$H |
| 65 | OH | 3 | 0 | — | SO$_3$H (6) | NH (3) | Cl | " | SO$_2$CH$_2$CH$_2$OSO$_3$H |
| 66 | OH | 3 | 0 | — | SO$_3$H (6) | NH (3) | F | " | SO$_2$CH=CH$_2$ |
| 67 | OH | 3 | 0 | — | SO$_3$H (3) | NH (3) | OH | " | SO$_2$CH$_2$CH$_2$OSO$_3$H |
| 68 | OH | 3 | 0 | — | SO$_3$H (6) | NH (3) | F | NHCH$_2$CH$_2$OCH$_2$CH$_2$ | SO$_2$CH=CH$_2$ |
| 69 | OH | 3 | 0 | — | SO$_3$H (6) | NH (3) | OH | NHCH$_2$CH$_2$OCH$_2$CH$_2$ | SO$_2$CH$_2$CH$_2$OSO$_3$H |
| 70 | OH | 2 | 1 | NH$_2$ | SO$_3$H (4) | NH (3) | Cl | | SO$_2$CH$_2$CH$_2$OSO$_3$H |
| 71 | OH | 2 | 1 | NHCH$_2$CH$_2$OH | H | NH (3) | Cl | | SO$_2$CH=CH$_2$ |
| 72 | OH | 2 | 1 | NHCH$_2$CH$_2$SO$_3$H | H | NH (3) | F | | SO$_2$CH$_2$CH$_2$OSO$_3$H |
| 73 | OH | 2 | 1 | H | | NH (3) | F | | SO$_2$CH$_2$CH$_2$OSO$_3$H |

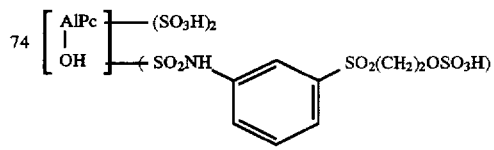

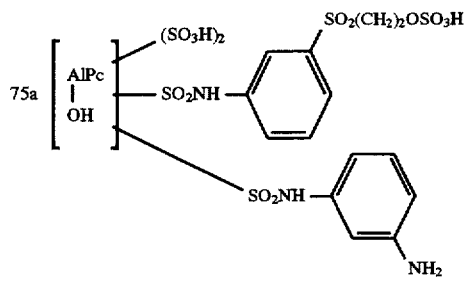

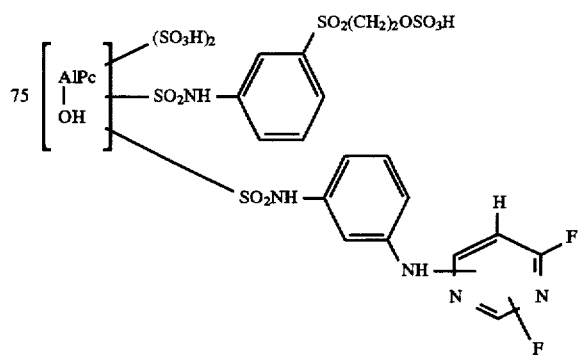

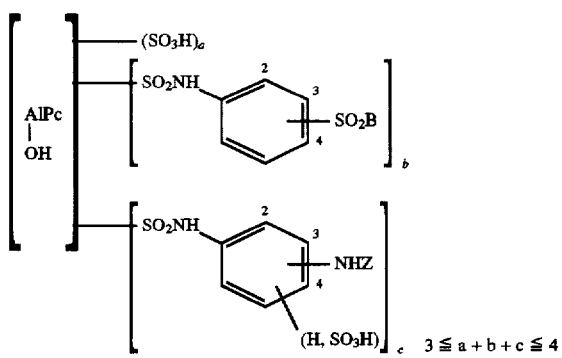

| Ex | a | SO$_2$B (Pos.) | H, SO$_3$H | NHZ (Pos.) |
|---|---|---|---|---|
| 75 | 2 | SO$_2$CH$_2$CH$_2$OSO$_3$H (3) | H | NHZ$_3$ (3) |
| 76 | 1 | SO$_2$CH$_2$CH$_2$OSO$_3$H (4) | H | NHZ$_3$ (3) |
| 77 | 2 | SO$_2$CH$_2$CH$_2$OSO$_3$H (4) | H | NHZ$_4$ (3) |
| 78 | 1 | SO$_2$CH$_2$CH$_2$OSO$_3$H (3) | SO$_3$H (4) | NHZ$_3$ (3) |
| 79 | 1 | SO$_2$CH$_2$CH$_2$OSO$_3$H (3) | SO$_3$H (4) | NHZ$_4$ (3) |
| 80 | 1.5 | SO$_2$CH$_2$CH$_2$OSO$_3$H (3) | H | NHZ$_3$ (3) |
| 81 | 1 | SO$_2$CH$_2$CH$_2$OSO$_3$H (3) | SO$_3$H (4) | NHZ$_8$ (3) |
| 82 | 1.5 | SO$_2$CH$_2$CH$_2$OSO$_3$H (3) | SO$_3$H (4) | NHZ$_4$ (3) |
| 83 | 2 | SO$_2$CH=CH$_2$ (4) | SO$_3$H (4) | NHZ$_4$ (3) |
| 84 | 2 | SO$_2$CH$_2$CH$_2$OSO$_3$H (3) | SO$_3$H (4) | NHZ$_5$ (3) |
| 85 | 2 | SO$_2$CH=CH$_2$ (3) | H | NHZ$_3$ (3) |

-continued

| | | | | |
|---|---|---|---|---|
| 86 | 2 | $SO_2CH=CH_2$ (3) | H | $NHZ_4$ (3) |
| 87 | 1.5 | $SO_2CH=CH_2$ (3) | $SO_3H$ (3) | $NHZ_5$ (4) |
| 88 | 1 | $SO_2CH_2CH_2OSO_3H$ (4) | $SO_3H$ (3) | $NHZ_5$ (4) |

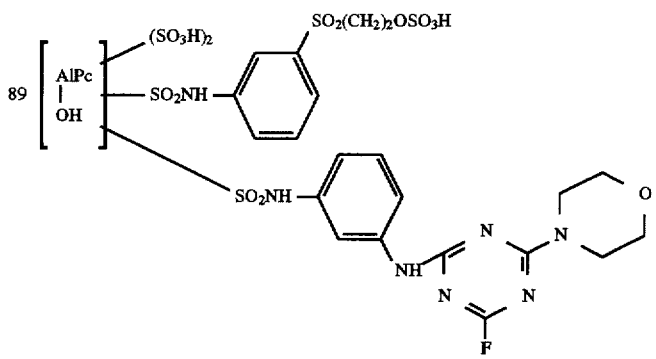

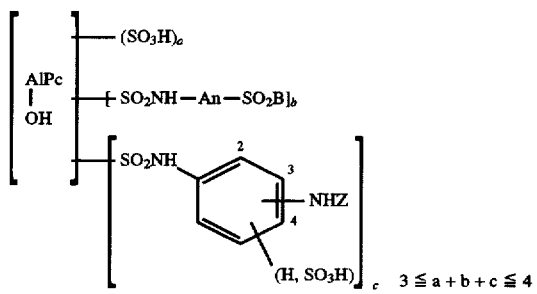

$3 \leq a+b+c \leq 4$

| Ex | a | $-SO_2B$ | $A_n$ | H, $SO_3H$ | $-NHZ$ |
|---|---|---|---|---|---|
| 90 | 1 | $-SO_2(CH_2)_2OSO_3H$ (3) | (m-xylylene) | $SO_3H$ (4) | $-NHZ_6$ (3) |
| 91 | 1 | $-SO_2CH=CH_2$ | $(CH_2)_2O(CH_2)_2$ | H | $-NHZ_7$ (3) |
| 92 | 2 | " | " | H | " |

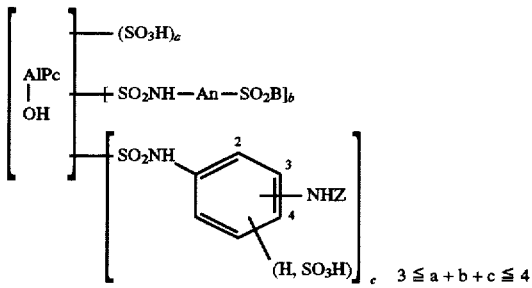

$3 \leq a+b+c \leq 4$

| Ex.- | a | $A_n$ | $SO_2B$ | H, $SO_3H$ | NHZ (Pos.) |
|---|---|---|---|---|---|
| 93 | 1 | $CH_2CH_2$ | $CH=CH_2$ | $SO_3H$ (4) | $NHZ_3$ (3) |
| 94 | 1 | $CH_2CH_2CH_2$ | $CH=CH_2$ | H | $NHZ_3$ (3) |
| 95 | 1.5 | $CH_2CH_2$ | $CH=CH_2$ | H | $NHZ_4$ (3) |
| 96 | 2 | $CH_2CH_2OCH_2CH_2$ | $CH_2CH_2Cl$ | H | $NHZ_3$ (3) |
| 97 | 1.5 | $CH_2CH_2CH_2$ | $CH_2CH_2Cl$ | $SO_3H$ (4) | $NHZ_5$ (3) |
| 98 | 2 | $CH_2CH_2OCH_2CH_2$ | $CH=CH_2$ | H | $NHZ_3$ (3) |
| 99 | 1 | $CH_2CH_2CH_2$ | $CH=CH_2$ | $SO_3H$ (4) | $NHZ_4$ (3) |
| 100 | 1.5 | $CH_2CH_2CH_2$ | $CH=CH_2$ | H | $NHZ_5$ (3) |

-continued
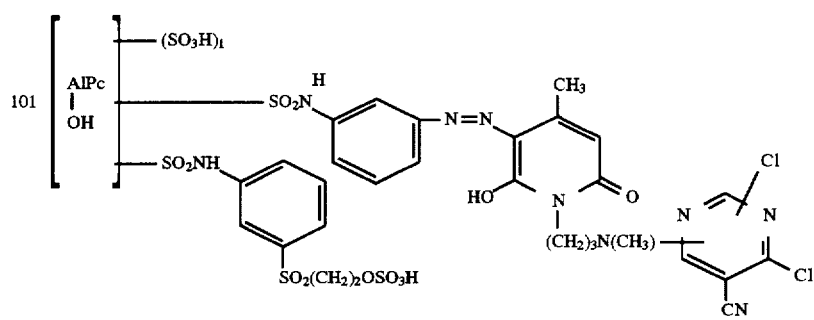
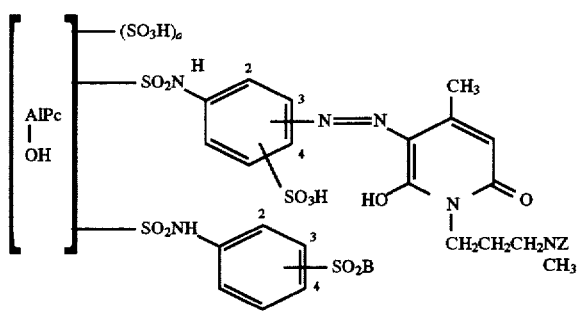
$3 \leq a+b+c \leq 4$
| Ex. | a | SO₃H (Pos.) | Z | —N=N (Pos.) | SO₂B (Pos.) |
|---|---|---|---|---|---|
| 102 | 1 | SO₃H (4) | $Z_5$ | 3 | SO₂CH₂CH₂OSO₃H (4) |
| 103 | 1.5 | SO₃H (4) | $Z_5$ | 3 | SO₂CH₂CH₂OSO₃H (3) |
| 104 | 2 | SO₃H (4) | $Z_5$ | 3 | SO₂CHCH₂ (4) |
| 105 | 2 | SO₃H (4) | $Z_5$ | 3 | SO₂CHCH₂ (5) |
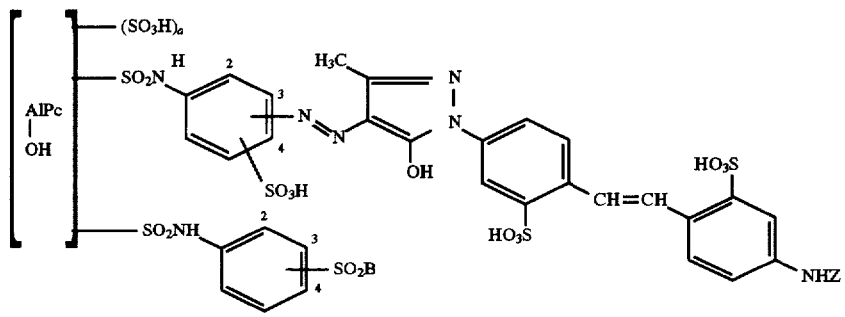
| Ex. | a | SO₃H (Pos.) | Z | —N=N (Pos.) | SO₂B (Pos.) |
|---|---|---|---|---|---|
| 106 | 1 | SO₃H (4) | $Z_9$ | 3 | SO₂CH₂CH₂OSO₃H (3) |
| 107 | 1 | SO₃H (4) | $Z_9$ | 3 | SO₂CH₂CH₂OSO₃H (4) |
| 108 | 1.5 | SO₃H (4) | $Z_9$ | 3 | SO₂CH₂CH₂OSO₃H (3) |
| 109 | 1.5 | SO₃H (4) | $Z_9$ | 3 | SO₂CH₂CH₂OSO₃H (3) |
| 110 | 2 | SO₃H (4) | $Z_5$ | 3 | SO₂CH₂CH₂OSO₃H (4) |
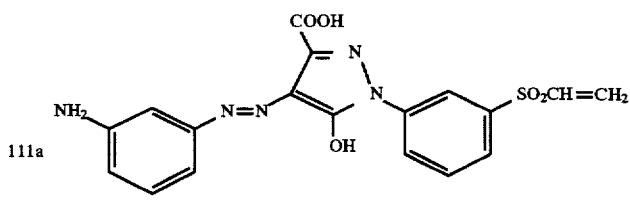

-continued
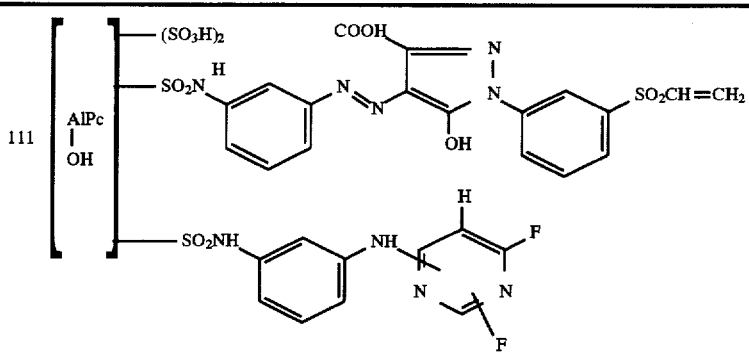
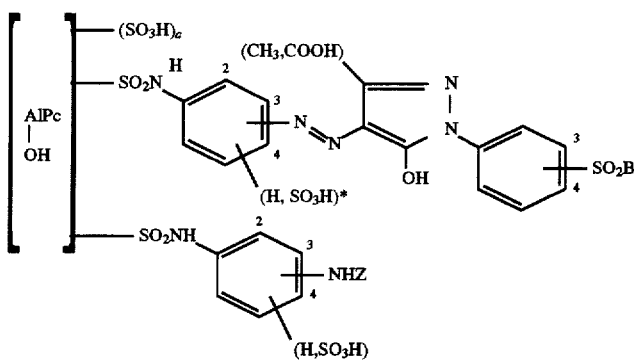
| Ex. | a | (H, SO$_3$H)* | CH$_3$, COOH | SO$_2$B (Pos.) | H, SO$_3$H (Pos.) | NHZ (Pos.) |
|---|---|---|---|---|---|---|
| 112 | 1 | SO$_3$H (4) | CH$_3$ | CH$_2$CH$_2$OSO$_3$H (4) | H | NHZ$_3$ (3) |
| 113 | 1.5 | SO$_3$H (4) | COOH | CH=CH$_2$ (4) | H | NHZ$_4$ (3) |
| 114 | 2 | H | CH$_3$ | CH$_2$CH$_2$OSO$_3$H (3) | H | NHZ$_3$ (3) |
| 115 | 1.5 | H | COOH | CH$_2$CH$_2$OSO$_3$H (4) | SO$_3$H (4) | NHZ$_5$ (3) |
| 116 | 2 | SO$_3$H (4) | CH$_3$ | CH$_2$CH$_2$OSO$_3$H | SO$_4$H (4) | NHZ$_3$ (3) |
\* \* \* \* \*